United States Patent
Brennan et al.

(10) Patent No.: US 10,273,281 B2
(45) Date of Patent: Apr. 30, 2019

(54) CD80 EXTRACELLULAR DOMAIN POLYPEPTIDES AND THEIR USE IN CANCER TREATMENT

(71) Applicant: Five Prime Therapeutics, Inc., South San Francisco, CA (US)

(72) Inventors: Thomas Brennan, Cupertino, CA (US); David Bellovin, South San Francisco, CA (US); David Busha, Sausalito, CA (US); Barbara Sennino, San Francisco, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/340,238

(22) Filed: Nov. 1, 2016

(65) Prior Publication Data

US 2017/0145071 A1 May 25, 2017

Related U.S. Application Data

(60) Provisional application No. 62/249,836, filed on Nov. 2, 2015, provisional application No. 62/373,654, filed on Aug. 11, 2016.

(51) Int. Cl.

| | | |
|---|---|---|
| *C07K 14/705* | (2006.01) | |
| *A61K 38/17* | (2006.01) | |
| *A61K 39/395* | (2006.01) | |
| *A61K 45/06* | (2006.01) | |
| *C07K 16/00* | (2006.01) | |
| *C07K 16/28* | (2006.01) | |
| *A61K 38/00* | (2006.01) | |

(52) U.S. Cl.
CPC .... *C07K 14/70532* (2013.01); *A61K 38/1774* (2013.01); *A61K 39/39558* (2013.01); *A61K 45/06* (2013.01); *C07K 16/00* (2013.01); *C07K 16/2803* (2013.01); *A61K 38/00* (2013.01); *C07K 2317/41* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,580,756 A | 12/1996 | Linsley et al. | |
| 6,071,716 A | 6/2000 | Freeman et al. | |
| 6,130,316 A | 10/2000 | Freeman et al. | |
| 6,218,510 B1 | 4/2001 | Sharpe et al. | |
| 6,294,660 B1 | 9/2001 | Sharpe et al. | |
| 6,319,709 B1 | 11/2001 | Ostrand-Rosenberg et al. | |
| 6,451,305 B1 | 9/2002 | Boussiotis et al. | |
| 6,491,925 B2 | 12/2002 | Selvaraj et al. | |
| 6,641,809 B1 | 11/2003 | Linsley et al. | |
| 6,653,444 B1 | 11/2003 | Freeman et al. | |
| 6,824,779 B1 | 11/2004 | Freeman et al. | |
| 6,887,471 B1 | 5/2005 | Linsley et al. | |
| 7,011,833 B1 | 3/2006 | Sturmhoefel et al. | |
| 7,064,111 B1 | 6/2006 | Todo et al. | |
| 7,070,776 B1 | 7/2006 | Linsley et al. | |
| 7,183,376 B2 | 2/2007 | Punnonen et al. | |
| 7,229,628 B1 | 6/2007 | Allison et al. | |
| 7,311,910 B2 | 12/2007 | Linsley et al. | |
| 7,619,078 B2 | 11/2009 | Sharpe et al. | |
| 7,678,890 B2 * | 3/2010 | Bosch | C07K 14/71 530/387.3 |
| 7,794,718 B2 * | 9/2010 | Karrer | C07K 14/70521 424/134.1 |
| 7,968,680 B2 | 6/2011 | Green et al. | |
| 8,114,845 B2 | 2/2012 | Langermann et al. | |
| 8,268,788 B2 | 9/2012 | Epstein et al. | |
| 8,956,619 B2 | 2/2015 | Ostrand-Rosenberg | |
| 8,969,526 B2 | 3/2015 | Baehner et al. | |
| 9,220,728 B2 | 12/2015 | Sadelain et al. | |
| 9,308,236 B2 | 4/2016 | Miller et al. | |
| 9,567,642 B2 | 2/2017 | Feldser et al. | |
| 9,650,429 B2 | 5/2017 | Ostrand-Rosenberg et al. | |
| 9,834,604 B2 | 12/2017 | Zhu et al. | |
| 9,879,046 B2 | 1/2018 | Miller et al. | |
| 2002/0147326 A1 | 10/2002 | Chaikin et al. | |
| 2004/0236091 A1 | 11/2004 | Chicz et al. | |
| 2009/0041790 A1 | 2/2009 | Rusnak et al. | |
| 2011/0044953 A1 | 2/2011 | Allison et al. | |
| 2011/0223188 A1 | 9/2011 | Langermann | |
| 2013/0017199 A1 | 1/2013 | Langermann | |
| 2014/0377253 A1 | 12/2014 | Harding et al. | |
| 2016/0251437 A1 | 9/2016 | Dong et al. | |

(Continued)

FOREIGN PATENT DOCUMENTS

| | | |
|---|---|---|
| EP | 2 662 383 A1 | 11/2013 |
| EP | 2856876 B1 | 1/2018 |

(Continued)

OTHER PUBLICATIONS

Haile et al. (J. Immunol. 191(5)L 2829-2836, Sep. 1, 2013).*
Lechner et al. J. Immunother. 36(9): 447-489, 2013.*
Czajkowsky, Daniel M. et al. "Fc-fusion proteins: new developments and future perspectives" EMBO Molecular Medicine, 4(10): 1015-1028 (2012).
Haile, S.T. et al. "A Soluble Form of CD80 Enhances Antitumor Immunity by Neutralizing Programmed Death Ligan-1 and Simultaneously Providing Costimulation" Cancer Immunology Research, 2(7): 610-615 (2014).
Haile, S.T. et al. "Soluble CD80 Restores T Cell Activation and Overcomes Tumor Cell Programmed Death Ligand 1-Mediated Immune Suppression" The Journal of Immunology, 191(5):2829-2836 (2013).

(Continued)

*Primary Examiner* — Alana Harris Dent
(74) *Attorney, Agent, or Firm* — Sterne, Kessler, Goldstein & Fox P.L.L.C.

(57) ABSTRACT

This application relates to CD80 (B7-1) extracellular domain (ECD) polypeptides and CD80-ECD fusion molecules and their use in treatment of cancer, both alone and in combination with other therapeutic agents, such as immune stimulating agents such as PD-1/PD-L1 inhibitors.

40 Claims, 11 Drawing Sheets

Specification includes a Sequence Listing.

(56) References Cited

U.S. PATENT DOCUMENTS

| | | |
|---|---|---|
| 2017/0044268 A1 | 2/2017 | Gurney et al. |
| 2017/0226181 A1 | 8/2017 | Ostrand-Rosenberg et al. |
| 2017/0274073 A1 | 9/2017 | Grogan et al. |
| 2017/0320959 A1 | 11/2017 | Swanson et al. |
| 2018/0044400 A1 | 2/2018 | Kaempfer et al. |
| 2018/0117145 A1 | 5/2018 | Selvaraj et al. |
| 2018/0244749 A1 | 8/2018 | Swanson et al. |

FOREIGN PATENT DOCUMENTS

| | | |
|---|---|---|
| EP | 3330290 A1 | 6/2018 |
| EP | 3348571 A1 | 7/2018 |
| WO | WO-1998058965 A1 | 12/1998 |
| WO | WO 2003/039486 A2 | 5/2003 |
| WO | WO 2004/029197 A2 | 4/2004 |
| WO | WO-2008037080 A1 | 4/2008 |
| WO | WO 2008/119071 A1 | 10/2008 |
| WO | WO 2008/121821 A1 | 10/2008 |
| WO | WO 2009/089149 A1 | 7/2009 |
| WO | WO-2013019906 A1 | 2/2013 |
| WO | WO 2014/151006 A2 | 9/2014 |
| WO | WO-2015200119 A1 | 12/2015 |
| WO | WO-2016161239 A1 | 10/2016 |
| WO | WO-2016168771 A2 | 10/2016 |
| WO | WO 2016/174200 A1 | 11/2016 |
| WO | WO-2017019846 A1 | 2/2017 |
| WO | WO 2017/042816 A1 | 3/2017 |
| WO | WO-2017048878 A1 | 3/2017 |
| WO | WO-2017079117 A1 | 5/2017 |
| WO | WO-2017103291 A1 | 6/2017 |
| WO | WO-2017144681 A1 | 8/2017 |
| WO | WO-2017149150 A1 | 9/2017 |
| WO | WO-2017151818 A2 | 9/2017 |
| WO | WO-2017181152 A2 | 10/2017 |
| WO | WO-2017201210 A1 | 11/2017 |
| WO | WO-2017201352 A1 | 11/2017 |
| WO | WO-2018064190 A1 | 4/2018 |
| WO | WO-2018075978 A1 | 4/2018 |

OTHER PUBLICATIONS

Ostrand-Rosenberg, Suzanne et al. "Novel strategies for inhibiting PD-1 pathway-mediated immune suppression while simultaneously delivering activating signals to tumor-reactive T cells" Cancer Immunology, Immunotherapy, 64(10): 1287-1293 (2015).

Solá, Ricardo J. "Glycosylation of Therapeutics Proteins", Biodrugs, 24(1): 9-21 (2010).

International Preliminary Report on Patentability for Application No. PCT/US2016/059838, International Bureau of WIPO, Switzerland, dated May 8, 2018, 11 pages.

Linsley, P.S., et al., "Binding of the B Cell Activation Antigen B7 to CD28 Costimulates T Cell Proliferation and Interleukin 2 mRNA Accumulation," J. Exp. Med. 173:721-730, Rockefeller University Press, United States (Mar. 1991).

Collins, M., et al., "The B7 family of immune-regulatory ligands," Genome Biology 6(6):223, BioMed Central Ltd., England, 7 pages (2005).

Felix, J., et al., "Ipilimumab reshapes T cell memory subsets in melanoma patients with clinical response," Oncoimmunology 5(7):e1136045, Taylor & Francis Group, England, 10 pages (Feb. 18, 2016).

Findlay, L., et al., "Improved in vitro methods to predict the in vivo toxicity in man of therapeutic monoclonal antibodies including TGN1412," Journal of Immunological Methods 352(1-2):1-12, Elsevier B.V., Netherlands (2010).

Greaves, P. and Gribben, J.G., "The role of B7 family molecules in hematologic malignancy," Blood 121(5):734-744, American Society of Hematology, United States (2013).

Klebanoff, C.A., et al., "Central memory self/tumor-reactive CD8[+] T cells confer superior antitumor immunity compared with effector memory T cells," Proc Natl Acad Sci USA 102(27):9571-9576, National Academy of Sciences, United States (2005).

Mahnke, Y.D., et al., "The who's who of T-cell differentiation: Human memory T-cell subsets," Eur J Immunol. 43(11):2797-2809, Wiley-VCH Verlag GmbH & Co. KGaA, Germany (2013).

Ostrand-Rosenberg, S., et al., "The programmed death-1 immune-suppressive pathway: barrier to antitumor immunity," The Journal of Immunology 193(8):3835-3841, The American Association of Immunologists, Inc., United States (2014).

Peach, R.J., et al., "Both extracellular immunoglobin-like domains of CD80 contain residues critical for binding T cell surface receptors CTLA-4 and CD28," The Journal of Biological Chemistry 270(36):21181-21187, The American Society for Biochemistry and Molecular Biology, Inc., United States (1995).

Vessillier, S., et al., "Cytokine release assays for the prediction of therapeutic mAb safety in first-in man trials—Whole blood cytokine release assays are poorly predictive for TGN1412 cytokine storm," Journal of Immunological Methods 424:43-52, Elsevier B.V., Netherlands (May 7, 2015).

Weber, J.S., et al., "Ipilimumab increases activated T cells and enhances humoral immunity in patients with advanced melanoma," J Immunother. 35(1):89-97 (2012).

Alegre, M-L., et al., "T-cell regulation by CD28 and CTLA-4," Nature Reviews Immunology 1:220-228, Macmillan Magazines Ltd., England (2001).

Bhatia, S., et al., "Dynamic Equilibrium of B7-1 Dimers and Monomers Differentially Affects Immunological Synapse Formation and T Cell Activation in Response to TCR/CD28 Stimulation," The Journal of Immunology 184(4):1821-1828, The American Association of Immunologists, Inc., United States (2010).

Dalal, S.P., et al., "Mutated CD80 may facilitate T-cell activation by inhibiting PDL1-PD1 suppression and by costimulating," Cancer Res 73(8 Suppl):Abstract 1264, in Proceedings of the 104th Annual Meeting of the American Association for Cancer Research, Apr. 6-10, American Association for Cancer Research, United States (2013).

Eastwood, D., et al., "Monoclonal antibody TGN1412 trial failure explained by species differences in CD28 expression on CD4[+] effector memory T-cells," British Journal of Pharmacology 161:512-526, The British Pharmacological Society, England (2010).

Freeman, G.J., et al., "B7-1 and B7-2 do not deliver identical costimulatory signals, since B7-2 but not B7-1 preferentially costimulates the initial production of IL-4," Immunity 2(5):523-532, Cell Press, United States (1995).

Girard, T., et al., "CD80 and CD86 IgC domains are important for quaternary structure, receptor binding and co-signaling function," Immunology Letters 161:65-75, Elsevier B.V., Netherlands (2014).

Gogishvili, T., et al., "Rapid Regulatory T-Cell Response Prevents Cytokine Storm in CD28 Superagonist Treated Mice," PLoS ONE 4(2):e4643, Public Library of Science, United States, 9 pages (2009).

Hünig, T., "The storm has cleared: lessons from the CD28 superagonist TGN1412 trial," Nature Reviews Immunology 12:317-318, Macmillan Publishers Limited, England (2012).

Kakoulidou, M., et al., "Human Soluble CD80 is Generated by Alternative Splicing, and Recombinant Soluble CD80 Binds to CD28 and CD152 Influencing T-cell Activation," Scandinavian Journal of Immunology 66:529-537, Blackwell Publishing Ltd., England (2007).

Lechner, M.G., et al., "Chemokines, costimulatory molecules and fusion proteins for the immunotherapy of solid tumors," Immunotherapy 3(11):1317-1340, Future Medicine, England (2011).

Liu, A., et al., "Combination B7-Fc Fusion Protein Treatment and Treg Cell Depletion Therapy," Clinical Cancer Research 11(23):8492-8502, American Association for Cancer Research, United States (2005).

Park, H-M., et al., "CD4 T-cells transduced with CD80 and 4-1BBL mRNA induce long-term CD8 T-cell responses resulting in potent antitumor effects," Vaccine 32:6919-6926, Elsevier Ltd., England (2014).

Pützer, B.M., et al., "Interleukin 12 and B7-1 costimulatory molecule expressed by an adenovirus vector act synergistically to facilitate tumor regression," Proc. Natl. Acad. Sci. USA 94:10889-10894, The National Academy of Sciences, United States (1997).

(56) References Cited

OTHER PUBLICATIONS

Runyon, K., et al., "The combination of chemotherapy and systemic immunotherapy with soluble B7-immunoglobulin G leads to cure of murine leukemia and lymphoma and demonstration of tumor-specific memory responses," *Blood* 97:2420-2426, The American Society of Hematology, United States (2001).

Sansom, D.M., "CD28, CTLA-4 and their ligands who does what and to whom?" *Immunology* 101:169-177, Blackwell Science Ltd., England (2000).

Sturmhoefel, K., et al., "Potent Activity of Soluble B7-IgG Fusion Proteins in Therapy of Established Tumors and as Vaccine Adjuvant," *Cancer Research* 59:4964-4972, American Association for Cancer Research, United States (1999).

Walker, L.S.K. and Sansom, D.M., "The emerging role of CTLA4 as a cell-extrinsic regulator of T cell responses," *Nature Reviews Immunology* 11:852-863, Macmillan Publishers Limited, England (2011).

Yamaguchi, N., et al., "Induction of Tumor Regression by Administration of B7-Ig Fusion Proteins: Mediation by Type 2 $CD8^+$ T Cells and Dependence on IL-4 Production," *The Journal of Immunology* 172:1347-1354, The American Association of Immunologists, Inc., United States (2004).

Yao, S., et al., "Advances in targeting cell surface signalling molecules for immune modulation," *Nature Reviews Drug Discovery* 12:130-146, Macmillan Publishers Limited, England (2013).

Barbee, S., et al., "FPT155, a novel therapeutic CD 80-Fc fusion protein, with potent anti-tumor activity in preclinical models", presented at 2017 AACR-EORTC International Conference on Molecular Targets and Cancer Therapeutics, Oct. 30, 2017, 1 page, California, United States.

\* cited by examiner

```
                        SEQUENCE LISTING

<160> NUMBER OF SEQ ID NOS: 25

<210> SEQ ID NO 1
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Human CD80 precursor (with signal sequence)

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 2
<211> LENGTH: 306
<212> TYPE: PRT
<213> ORGANISM: Mus musculus
<220> FEATURE:
<221> NAME/KEY: MISC_FEATURE
<222> LOCATION: (1)..(306)
```

<223> OTHER INFORMATION: Mouse CD80 precursor (with signal sequence)

<400> SEQUENCE: 2

```
Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305
```

<210> SEQ ID NO 3
<211> LENGTH: 222
<212> TYPE: PRT
<213> ORGANISM: Homo sapiens
<220> FEATURE:
<221> NAME/KEY: MISC_FEATURE
<222> LOCATION: (1)..(222)
<223> OTHER INFORMATION: Human CD80 Isoform 2 (without signal sequence)

<400> SEQUENCE: 3

```
Val Ile His Val Thr Lys Glu Val Lys Glu Val Ala Thr Leu Ser Cys
1               5                   10                  15
```

```
Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
 50                  55                  60

Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Ser Phe Ala Pro Arg Cys Arg Glu Arg
        195                 200                 205

Arg Arg Asn Glu Arg Leu Arg Arg Glu Ser Val Arg Pro Val
210                 215                 220

<210> SEQ ID NO 4
<211> LENGTH: 128
<212> TYPE: PRT
<213> ORGANISM: Homo sapiens
<220> FEATURE:
<221> NAME/KEY: MISC_FEATURE
<222> LOCATION: (1)..(128)
<223> OTHER INFORMATION: Human CD80 Isoform 2 (without signal sequence)

<400> SEQUENCE: 4

Val Ile His Val Thr Lys Glu Val Lys Glu Val Ala Thr Leu Ser Cys
 1               5                  10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
 50                  55                  60

Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Gly Phe Ala Pro Arg Cys Arg
            100                 105                 110

Glu Arg Arg Arg Asn Glu Arg Leu Arg Arg Glu Ser Val Arg Pro Val
        115                 120                 125

<210> SEQ ID NO 5
<211> LENGTH: 208
<212> TYPE: PRT
```

<213> ORGANISM: Homo sapiens
<220> FEATURE:
<221> NAME/KEY: MISC_FEATURE
<222> LOCATION: (1)..(208)
<223> OTHER INFORMATION: Human CD80 ECD sequence (without signal
      sequence)

<400> SEQUENCE: 5

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 6
<211> LENGTH: 209
<212> TYPE: PRT
<213> ORGANISM: Mus musculus
<220> FEATURE:
<221> NAME/KEY: MISC_FEATURE
<222> LOCATION: (1)..(209)
<223> OTHER INFORMATION: Mouse CD80 ECD sequence (without signal
      sequence)

<400> SEQUENCE: 6

Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
    50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

```
Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
    130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
            180                 185                 190

Glu Asp Phe Thr Trp Glu Lys Pro Pro Glu Asp Pro Pro Asp Ser Lys
        195                 200                 205

Asn

<210> SEQ ID NO 7
<211> LENGTH: 34
<212> TYPE: PRT
<213> ORGANISM: Artificial Sequence
<220> FEATURE:
<223> OTHER INFORMATION: Human CD80 signal sequence

<400> SEQUENCE: 7

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly

<210> SEQ ID NO 8
<211> LENGTH: 37
<212> TYPE: PRT
<213> ORGANISM: Artificial Sequence
<220> FEATURE:
<223> OTHER INFORMATION: Mouse CD80 signal sequence

<400> SEQUENCE: 8

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp
            35

<210> SEQ ID NO 9
<211> LENGTH: 232
<212> TYPE: PRT
<213> ORGANISM: Artificial Sequence
<220> FEATURE:
<223> OTHER INFORMATION: Fc C237S

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 10
<211> LENGTH: 228
<212> TYPE: PRT
<213> ORGANISM: Artificial Sequence
<220> FEATURE:
<223> OTHER INFORMATION: Fc

<400> SEQUENCE: 10

Glu Arg Lys Cys Cys Val Glu Cys Pro Pro Cys Pro Ala Pro Pro Val
  1               5                  10                  15

Ala Gly Pro Ser Val Phe Leu Phe Pro Pro Lys Pro Lys Asp Thr Leu
                 20                  25                  30

Met Ile Ser Arg Thr Pro Glu Val Thr Cys Val Val Val Asp Val Ser
             35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175
```

```
Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 11
<211> LENGTH: 229
<212> TYPE: PRT
<213> ORGANISM: Artificial Sequence
<220> FEATURE:
<223> OTHER INFORMATION: Fc

<400> SEQUENCE: 11

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 232
<212> TYPE: PRT
<213> ORGANISM: Artificial Sequence
<220> FEATURE:
<223> OTHER INFORMATION: Human IgG1 Fc L234F, L235E, P331S mutant

<400> SEQUENCE: 12

Glu Pro Lys Ser Ser Asp Lys Thr His Thr Cys Pro Cys Pro Ala
1               5                   10                  15
```

```
Pro Glu Phe Glu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 13
<211> LENGTH: 232
<212> TYPE: PRT
<213> ORGANISM: Artificial Sequence
<220> FEATURE:
<223> OTHER INFORMATION: Human IgG1 Fc N297 mutant

<400> SEQUENCE: 13

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Gly Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140
```

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 14
<211> LENGTH: 232
<212> TYPE: PRT
<213> ORGANISM: Artificial Sequence
<220> FEATURE:
<223> OTHER INFORMATION: Fc human IgG1

<400> SEQUENCE: 14

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 15
<211> LENGTH: 279
<212> TYPE: PRT
<213> ORGANISM: Artificial Sequence

```
<220> FEATURE:
<223> OTHER INFORMATION: Fc human IgG3

<400> SEQUENCE: 15

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 16
<211> LENGTH: 229
<212> TYPE: PRT
<213> ORGANISM: Artificial Sequence
<220> FEATURE:
<223> OTHER INFORMATION: Fc human IgG4

<400> SEQUENCE: 16

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

```
                50                  55                  60
Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                     85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 17
<211> LENGTH: 442
<212> TYPE: PRT
<213> ORGANISM: Mus musculus
<220> FEATURE:
<221> NAME/KEY: MISC_FEATURE
<222> LOCATION: (1)..(442)
<223> OTHER INFORMATION: Mouse CD80 ECD mouse Fc IgG2a

<400> SEQUENCE: 17

Val Asp Glu Gln Leu Ser Lys Ser Val Lys Asp Lys Val Leu Leu Pro
 1               5                  10                  15

Cys Arg Tyr Asn Ser Pro His Glu Asp Glu Ser Glu Asp Arg Ile Tyr
                20                  25                  30

Trp Gln Lys His Asp Lys Val Val Leu Ser Val Ile Ala Gly Lys Leu
            35                  40                  45

Lys Val Trp Pro Glu Tyr Lys Asn Arg Thr Leu Tyr Asp Asn Thr Thr
        50                  55                  60

Tyr Ser Leu Ile Ile Leu Gly Leu Val Leu Ser Asp Arg Gly Thr Tyr
 65                  70                  75                  80

Ser Cys Val Val Gln Lys Lys Glu Arg Gly Thr Tyr Glu Val Lys His
                 85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
    130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175
```

```
Asn His Thr Ile Lys Cys Leu Ile Lys Tyr Gly Asp Ala His Val Ser
            180                 185                 190

Glu Asp Phe Thr Trp Glu Lys Pro Glu Asp Pro Asp Ser Lys
        195                 200                 205

Asn Glu Pro Arg Gly Pro Thr Ile Lys Pro Cys Pro Pro Cys Lys Cys
210                 215                 220

Pro Ala Pro Asn Leu Leu Gly Gly Pro Ser Val Phe Ile Phe Pro Pro
225                 230                 235                 240

Lys Ile Lys Asp Val Leu Met Ile Ser Leu Ser Pro Ile Val Thr Cys
                245                 250                 255

Val Val Val Asp Val Ser Glu Asp Asp Pro Asp Val Gln Ile Ser Trp
                260                 265                 270

Phe Val Asn Asn Val Glu Val His Thr Ala Gln Thr Gln Thr His Arg
            275                 280                 285

Glu Asp Tyr Asn Ser Thr Leu Arg Val Val Ser Ala Leu Pro Ile Gln
        290                 295                 300

His Gln Asp Trp Met Ser Gly Lys Glu Phe Lys Cys Lys Val Asn Asn
305                 310                 315                 320

Lys Asp Leu Pro Ala Pro Ile Glu Arg Thr Ile Ser Lys Pro Lys Gly
                325                 330                 335

Ser Val Arg Ala Pro Gln Val Tyr Val Leu Pro Pro Glu Glu Glu
                340                 345                 350

Met Thr Lys Lys Gln Val Thr Leu Thr Cys Met Val Thr Asp Phe Met
            355                 360                 365

Pro Glu Asp Ile Tyr Val Glu Trp Thr Asn Asn Gly Lys Thr Glu Leu
        370                 375                 380

Asn Tyr Lys Asn Thr Glu Pro Val Leu Asp Ser Asp Gly Ser Tyr Phe
385                 390                 395                 400

Met Tyr Ser Lys Leu Arg Val Glu Lys Lys Asn Trp Val Glu Arg Asn
                405                 410                 415

Ser Tyr Ser Cys Ser Val Val His Glu Gly Leu His Asn His His Thr
                420                 425                 430

Thr Lys Ser Phe Ser Arg Thr Pro Gly Lys
            435                 440

<210> SEQ ID NO 18
<211> LENGTH: 441
<212> TYPE: PRT
<213> ORGANISM: Mus musculus
<220> FEATURE:
<221> NAME/KEY: MISC_FEATURE
<222> LOCATION: (1)..(441)
<223> OTHER INFORMATION: Mouse CD80 ECD Human Fc IgG1 WT

<400> SEQUENCE: 18

Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
                20                  25                  30

Trp Gln Lys His Asp Lys Val Val Leu Ser Val Ile Ala Gly Lys Leu
            35                  40                  45

Lys Val Trp Pro Glu Tyr Lys Asn Arg Thr Leu Tyr Asp Asn Thr Thr
        50                  55                  60

Tyr Ser Leu Ile Ile Leu Gly Leu Val Leu Ser Asp Arg Gly Thr Tyr
65                  70                  75                  80
```

```
Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
    130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
            180                 185                 190

Glu Asp Phe Thr Trp Glu Lys Pro Pro Glu Asp Pro Pro Asp Ser Lys
        195                 200                 205

Asn Glu Pro Lys Ser Ser Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 19
<211> LENGTH: 441
<212> TYPE: PRT
<213> ORGANISM: Mus musculus
<220> FEATURE:
<221> NAME/KEY: MISC_FEATURE
<222> LOCATION: (1)..(441)
<223> OTHER INFORMATION: Mouse CD80 ECD Fc IgG1 MT (234, 235, 331)
```

<400> SEQUENCE: 19

```
Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
            180                 185                 190

Glu Asp Phe Thr Trp Glu Lys Pro Pro Glu Asp Pro Pro Asp Ser Lys
        195                 200                 205

Asn Glu Pro Lys Ser Ser Asp Lys Thr His Thr Cys Pro Pro Cys Pro
210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Ser Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

```
Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 20
<211> LENGTH: 440
<212> TYPE: PRT
<213> ORGANISM: Homo sapiens
<220> FEATURE:
<221> NAME/KEY: MISC_FEATURE
<222> LOCATION: (1)..(440)
<223> OTHER INFORMATION: Human CD80 ECD Human Fc IgG1 WT

<400> SEQUENCE: 20

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Glu Pro Lys Ser Ser Asp Lys Thr His Thr Cys Pro Pro Cys Pro Ala
    210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320
```

```
Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys
        435                 440

<210> SEQ ID NO 21
<211> LENGTH: 440
<212> TYPE: PRT
<213> ORGANISM: Homo sapiens
<220> FEATURE:
<221> NAME/KEY: MISC_FEATURE
<222> LOCATION: (1)..(440)
<223> OTHER INFORMATION: Human CD80 ECD Human Fc IgG1 L234F, L235E,
      P331S MT

<400> SEQUENCE: 21

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Glu Pro Lys Ser Ser Asp Lys Thr His Thr Cys Pro Pro Cys Pro Ala
    210                 215                 220
```

Pro Glu Phe Glu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Ala
305                 310                 315                 320

Leu Pro Ala Ser Ile Glu Lys Thr Ile Ser Lys Ala Lys Gly Gln Pro
            325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Pro Gly Lys
        435                 440

<210> SEQ ID NO 22
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: human PD-1 precursor (with signal sequence)

<400> SEQUENCE: 22

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val

```
                  130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                  165                 170                 175

Leu Leu Gly Ser Leu Val Leu Leu Val Trp Val Leu Ala Val Ile Cys
                  180                 185                 190

Ser Arg Ala Ala Arg Gly Thr Ile Gly Ala Arg Arg Thr Gly Gln Pro
                  195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                  245                 250                 255

Met Gly Thr Ser Ser Pro Ala Arg Arg Gly Ser Ala Asp Gly Pro Arg
                  260                 265                 270

Ser Ala Gln Pro Leu Arg Pro Glu Asp Gly His Cys Ser Trp Pro Leu
                  275                 280                 285
```

<210> SEQ ID NO 23
<211> LENGTH: 268
<212> TYPE: PRT
<213> ORGANISM: Homo sapiens
<220> FEATURE:
<221> NAME/KEY: MISC_FEATURE
<222> LOCATION: (1)..(268)
<223> OTHER INFORMATION: human PD-1 (mature, without signal sequence)

<400> SEQUENCE: 23

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                  20                  25                  30

Thr Cys Ser Phe Ser Asn Thr Ser Glu Ser Phe Val Leu Asn Trp Tyr
                  35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                  85                  90                  95

Asp Ser Gly Thr Tyr Leu Cys Gly Ala Ile Ser Leu Ala Pro Lys Ala
                  100                 105                 110

Gln Ile Lys Glu Ser Leu Arg Ala Glu Leu Arg Val Thr Glu Arg Arg
                  115                 120                 125

Ala Glu Val Pro Thr Ala His Pro Ser Pro Ser Pro Arg Pro Ala Gly
                  130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                  165                 170                 175

Arg Gly Thr Ile Gly Ala Arg Arg Thr Gly Gln Pro Leu Lys Glu Asp
                  180                 185                 190

Pro Ser Ala Val Pro Val Phe Ser Val Asp Tyr Gly Glu Leu Asp Phe
                  195                 200                 205
```

-continued

Gln Trp Arg Glu Lys Thr Pro Glu Pro Pro Val Pro Cys Val Pro Glu
        210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
            245                 250                 255

Leu Arg Pro Glu Asp Gly His Cys Ser Trp Pro Leu
        260                 265

<210> SEQ ID NO 24
<211> LENGTH: 290
<212> TYPE: PRT
<213> ORGANISM: Homo sapiens
<220> FEATURE:
<221> NAME/KEY: MISC_FEATURE
<222> LOCATION: (1)..(290)
<223> OTHER INFORMATION: human PD-L1 precursor (with signal sequence)

<400> SEQUENCE: 24

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

```
Glu Thr
    290

<210> SEQ ID NO 25
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)
<223> OTHER INFORMATION: human PD-L1 (mature, without signal sequence)

<400> SEQUENCE: 25

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270
```

CD80 EXTRACELLULAR DOMAIN POLYPEPTIDES AND THEIR USE IN CANCER TREATMENT

CROSS-REFERENCE TO RELATED APPLICATIONS

This application claims priority to U.S. Provisional Patent Application Nos. 62/373,654, filed Aug. 11, 2016, and 62/249,836, filed Nov. 2, 2015, both of which are incorporated herein by reference in their entirety.

FIELD

This application relates to CD80 (B7-1) extracellular domain (ECD) polypeptides and CD80-ECD fusion molecules and their use in treatment of cancer, both alone and in combination with other therapeutic agents, such as immune stimulating agents such as PD-1/PD-L1 inhibitors.

BACKGROUND

CD80, also known as B7-1, is one of the B7 family of membrane-bound proteins involved in immune regulation by delivering costimulatory or coinhibitory responses through their ligand binding activities. Other members of the B7 family of proteins include CD86 (B7-2), inducible costimulator ligand (ICOS-L), programmed death-1 ligand (PD-L1; B7-H1), programmed death-2 ligand (PD-L2; B7-H2), B7-H3, and B7-H4. CD80 is a transmembrane protein expressed on the surface of T cells, B cells, dendritic cells and monocytes, and binds to the receptors CD28, CTLA4 (CD152), and PD-L1. CD80 and CD86 and their receptors CTLA4 and CD28 operate as a costimulatory-coinhibitory system, for example, to control T cell activation, expansion, differentiation, and survival. CD80 and CD86 interaction with CD28 results in costimulatory signals that lead, for example, to activation of T cell responses. CD80, in turn, stimulates upregulation of CTLA4, which, upon binding to CD80, acts to suppress the T cell response previously triggered by CD80/CD28 interactions. This feedback loop allows for fine control of immune responses.

CD80 has also been shown to interact with another B7 family member, PD-L1 with similar affinity to CD28, whereas CD86 does not interact with PD-L1. PD-L1 is one of two ligands for the programmed death-1 (PD-1) protein, which is also involved in T cell regulation. Specifically, expression of PD-1 on T cells may be induced after T cells have been activated, and binding of PD-1 to PD-L1 downregulates T cell activity by promoting T cell inactivation. Many tumor cells express PD-L1 on their surface, potentially leading to PD-1/PD-L1 interactions and the inhibition of T cell responses against the tumor. This observation has led to the development of inhibitors of the PD-1/PD-L1 interaction as cancer therapeutics designed to stimulate natural immune responses against tumors in patients.

Binding of CD80 to PD-L1 may serve as an alternative mechanism to block the PD-1/PD-L1 interaction and prevent inhibition of T cell responses at the site of a tumor. At the same time, however, increased levels of CD80 might also be available to bind to CD28 and to induce CTLA4, thus either inducing or inhibiting T cell responses. Some soluble forms of CD80 may also function to block CTLA4 activation by blocking endogenous CD80 activity. In addition, different soluble CD80 protein forms may have different effects on tumor growth through other interactions between the protein forms and tumor cells whose impact cannot be predicted in advance of testing. How various soluble forms of CD80 actually impact tumor growth in vivo has also not previously been directly tested. The present inventors have developed a set of CD80 extracellular domain (ECD) fusion molecules with particularly potent effects on tumor growth in a mouse model, both when administered alone, and when administered in conjunction with a PD-1/PD-L1 inhibitor. Based on the data shown in the working examples below, embodiments herein may provide superb therapeutic effects in cancer treatment.

SUMMARY

In some embodiments, a CD80 extracellular domain (ECD) polypeptide or a CD80 ECD fusion molecule is provided. In some embodiments, the fusion molecule comprises a CD80 ECD and at least one fusion partner, comprising an Fc domain of an immunoglobulin, such as a human IgG1, IgG2, IgG3, or IgG4, albumin, or a polymer such as PEG. In some embodiments, the CD80 ECD or CD80 ECD fusion molecule comprises a human CD80, such as that of SEQ ID NO:5, or a human CD80 ECD from CD80 isoform 2 or isoform 3 (SEQ ID NOs: 3 and 4). In some embodiments, the fusion molecule comprises an Fc domain, such as an Fc domain comprising a sequence selected from SEQ ID NOs: 9-16. In some embodiments, the fusion molecule comprises a human IgG1 Fc domain, such as one with a wild-type sequence such as that of SEQ ID NO:14, or alternatively, a mutant sequence with L234F, L235E, and P331S amino acid substitutions such as that of SEQ ID NO:12. In some embodiments, the CD80 ECD fusion molecule comprises an amino acid sequence selected from SEQ ID NO: 5, SEQ ID NO: 12, SEQ ID NO:14, SEQ ID NO: 20, and SEQ ID NO: 21. In some embodiments, the CD80 ECD fusion molecule fusion partner is directly attached to the C-terminal amino acid of the CD80 ECD amino acid sequence or to the N-terminal amino acid of the mature CD80 ECD amino acid sequence. In some embodiments, the CD80 ECD fusion molecule may be attached to the CD80 ECD through a linker peptide, such as a GS linker.

In some embodiments, the CD80 ECD fusion molecule has a sialic acid content of 10-60 mol sialic acid (SA)/mol protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some such embodiments, the CD80 ECD fusion molecule is a CD80 ECD Fc fusion, for example, with a wild-type Fc domain such as a human IgG1, IgG2, or IgG4 Fc domain, or, alternatively, an IgG1 Fc domain with substitutions at L234F, L235E, and P331S. In some embodiments, the CD80 ECD fusion molecule comprises an amino acid sequence selected from SEQ ID NO: 5, SEQ ID NO: 12, SEQ ID NO:14, SEQ ID NO: 20, and SEQ ID NO: 21. In some embodiments above, the fusion molecule has a greater percentage tumor growth inhibition in a mouse syngeneic or xenograft model, such as in a CT26 mouse model than a fusion molecule of identical amino acid sequence but a lower SA content. In some embodiments above, where the fusion molecule comprises at least 10 mol SA/mol protein, such as at least 15 mol SA/mol protein, such as at least 20 mol SA/mol protein, the fusion molecule has a greater percentage tumor growth inhibition in a mouse syngeneic or xenograft model, such as in a CT26 mouse model than a fusion molecule of identical amino acid sequence but having less than 10 mol SA/mol protein or less than 15 mol SA/mol protein or less than 20 mol SA/mol protein, respectively.

Some embodiments herein comprise a CD80 ECD fusion molecule wherein the molecule is capable of at least 50%, such as at least 60%, such as at least 70%, such as at least 80%, such as at least 90%, such as at least 95%, such as at least 98% tumor cell growth inhibition in at least one mouse syngeneic or xenograft cancer model, such as a CT26 model, over a period of at least ten days, such as at least two weeks, such as over a period of ten days to two weeks or two to three weeks, or at least three weeks.

In some embodiments, mice are given one to three doses of 0.3 to 3 mg/kg, such as 0.3 to 0.6 mg/kg, of the CD80 ECD Fc fusion molecule. In some such embodiments, the CD80 ECD fusion molecule also has a sialic acid content of 10-60 mol sialic acid (SA)/mol protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the CD80 ECD fusion molecule has an Fc as a fusion partner, such as a human IgG1, IgG2, or IgG4 Fc domain. In some embodiments, the CD80 ECD fusion molecule comprises an amino acid sequence selected from SEQ ID NO: 5, SEQ ID NO: 12, SEQ ID NO:14, SEQ ID NO: 20, and SEQ ID NO: 21. In some embodiments above where the fusion molecule comprises at least 10 mol SA/mol protein, such as at least 15 mol SA/mol protein, such as at least 20 mol SA/mol protein, the molecule has a greater percentage tumor growth inhibition in a mouse syngeneic or xenograft model, such as in a CT26 mouse model, than a fusion molecule of identical amino acid sequence but having less than 10 mol SA/mol protein or less than 15 mol SA/mol protein or less than 20 mol SA/mol protein, respectively. In some embodiments above where the fusion molecule comprises at least 10 mol SA/mol protein, such as at least 15 mol SA/mol protein, such as at least 20 mol SA/mol protein, the molecule has a greater percentage tumor growth inhibition in a mouse syngeneic or xenograft model, such as in a CT26 mouse model, after at least ten days or at least two weeks or at least three weeks, such as ten days to two weeks or two to three weeks, than an anti-CTLA4 antibody, such as anti-CTLA4 antibody clone 9D9.

In some of the above embodiments, the CD80 ECD Fc fusion molecule is also capable of inducing complete tumor regression in mice from the syngeneic or xenograft tumor model, such as a CT26 model.

Also provided herein are compositions comprising a CD80 ECD or CD80 ECD fusion molecule of any of the embodiments described above, and further comprising at least one pharmaceutically acceptable carrier. Some such compositions further comprise at least one additional therapeutic agent.

In some embodiments, the additional therapeutic agent comprises at least one immune stimulating agent. In some embodiments, the immune stimulating agent comprises a programmed cell death 1 (PD-1)/programmed cell death ligand 1 (PD-L1) inhibitor. The PD-1/PD-L1 inhibitor may be an antibody, such as an anti-PD-1 antibody or anti-PD-L1 antibody, a peptide or fusion molecule, or a small molecule.

In some embodiments, the PD-1/PD-L1 inhibitor is an anti-PD-1 antibody, such as an antibody comprising the heavy chain and light chain CDRs, or comprising the heavy and light chain variable regions, or comprising the full amino acid sequence, of an antibody selected from nivolumab, pidilizumab, and pembrolizumab. In some embodiments, the PD-1/PD-L1 inhibitor is an anti-PD-L1 antibody, such as an antibody comprising the heavy chain and light chain CDRs, the heavy and light chain variable regions, or the full amino acid sequence, of an antibody selected from BMS-936559, MPDL3280A, MEDI4736, and MSB0010718C.

In some embodiments, the PD-1/PD-L1 inhibitor is a PD-1 fusion molecule, such as AMP-224 or a polypeptide such as AUR-012.

Also included herein are methods of treating cancer in a subject comprising administering to the subject an effective amount of a CD80 ECD or CD80 ECD fusion protein or a composition from among the embodiments described above. In some embodiments, the cancer is a solid tumor. In some embodiments, the cancer is selected from colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer. In some embodiments, the cancer is recurrent or progressive after a therapy selected from surgery, chemotherapy, radiation therapy, or a combination thereof.

In some of the methods herein, the CD80 ECD, CD80 ECD fusion molecule, or composition is administered in combination with at least one additional therapeutic agent. In some such embodiments, the additional therapeutic agent may be packaged with the CD80 ECD or CD80 ECD fusion molecule as part of the same composition, e.g. mixed together in one composition or provided in separate containers, vials, or other packages. In some embodiments, the additional therapeutic agent comprises at least one immune stimulating agent. In some embodiments, the immune stimulating agent comprises a programmed cell death 1 (PD-1)/ programmed cell death ligand 1 (PD-L1) inhibitor. The PD-1/PD-L1 inhibitor may be an antibody, such as an anti-PD-1 antibody or anti-PD-L1 antibody, a peptide or fusion molecule, or a small molecule.

In some embodiments, the PD-1/PD-L1 inhibitor is an anti-PD-1 antibody, such as an antibody comprising the heavy chain and light chain CDRs, or comprising the heavy and light chain variable regions, or comprising the full amino acid sequence, of an antibody selected from nivolumab, pidilizumab, and pembrolizumab. In some embodiments, the PD-1/PD-L1 inhibitor is an anti-PD-L1 antibody, such as an antibody comprising the heavy chain and light chain CDRs, the heavy and light chain variable regions, or the full amino acid sequence, of an antibody selected from BMS-936559, MPDL3280A, MEDI4736, and MSB0010718C.

In some embodiments, the PD-1/PD-L1 inhibitor is a PD-1 fusion molecule, such as AMP-224 or a polypeptide such as AUR-012.

In some embodiments of the methods herein, the CD80 ECD or CD80 ECD fusion molecule and the additional therapeutic agent, such as an immune stimulating agent, such as a PD-1/PD-L1 inhibitor, may be administered concurrently or sequentially. In some cases, one or more doses of the PD-1/PD-L1 inhibitor are administered prior to administering the CD80 ECD or CD80 ECD fusion molecule. In some cases, the subject has received a complete course of immune stimulating agent, e.g., PD-1/PD-L1 inhibitor therapy prior to administration of the CD80 ECD or CD80 ECD fusion molecule. In some cases, the CD80 ECD or CD80 ECD fusion molecule is administered during a second course of immune stimulation agent, e.g. PD-1/PD-L1 inhibitor therapy. In some cases, the subject has received at least one, at least two, at least three, or at least four doses of the immune stimulating agent, such as PD-1/PD-L1 inhibitor prior to administration of the CD80 ECD or CD80 ECD fusion molecule. In some cases, at least one dose of the immune stimulating agent, e.g. PD-1/PD-L1 inhibitor is administered concurrently with the CD80 ECD or CD80 ECD fusion molecule.

In some embodiments, one or more doses of the CD80 ECD or CD80 ECD fusion molecule are administered prior to administering an additional therapeutic agent, such as an immune stimulating agent, such as a PD-1/PD-L1 inhibitor. In some such cases, the subject has received at least one, at least two, at least three, or at least four doses of the CD80 ECD or CD80 ECD fusion molecule prior to administration of an immune stimulating agent, e.g. a PD-1/PD-L1 inhibitor. In some cases, at least one dose of the CD80 ECD or CD80 ECD fusion molecule is administered concurrently with the immune stimulating agent, e.g. PD-1/PD-L1 inhibitor.

In any of the methods herein, the subject may be resistant to treatment with a PD-1/PD-L1 inhibitor. In some such cases, the subject has previously received PD-1/PD-L1 inhibitor therapy, while in other such cases, the subject has not previously received PD-1/PD-L1 inhibitor therapy but is identified as resistant through other means such as certain phenotypic traits.

In any of the above methods, the subject may be administered an additional therapeutic agent comprising at least one chemotherapy agent, growth inhibitory agent, anti-angiogenesis agent and/or anti-neoplastic composition, in addition to the CD80 ECD or CD80 ECD fusion molecule.

In some embodiments, the combination of the CD80 ECD or CD80 ECD fusion molecule and an immune stimulating agent, such as a PD-1/PD-L1 inhibitor that is administered to the subject has been shown to reduce or inhibit tumor growth in at least one mouse syngeneic or xenograft cancer model in a synergistic fashion compared to treatment with either the CD80 ECD or fusion molecule or the immune stimulating agent, such as the PD-1/PD-L1 inhibitor, given alone. In some embodiments, the mouse model is a colorectal cancer model with murine colorectal carcinoma CT26 cells. In other embodiments, the model may be an MC38 model or a B16 model.

In any of the above method embodiments, the CD80 ECD or CD80 ECD fusion molecule administered to the subject may inhibit tumor growth in at least one mouse syngeneic or xenograft cancer model over a period of 1 week, 10 days, 2 weeks, or 3 weeks, for example, by at least 10%, at least 20%, at least 30%, at least 40%, at least 50%, at least 60%, at least 70%, at least 80%, at least 90%, at least 95%, or at least 98%, or may inhibit growth of tumors by at least 10%, at least 20%, at least 30%, at least 40%, at least 50%, at least 60%, at least 70%, at least 80%, at least 90%, at least 95%, or at least 98% in a patient over a period of one month, two months, three months, six months, or one year. In any of the above method embodiments, administration of the CD80 ECD or CD80 ECD fusion molecule may reduce the volume of at least one tumor in an animal or human subject by at least 10%, at least 20%, at least 30%, at least 40%, at least 50%, at least 60%, at least 70%, at least 80%, at least 90%, at least 95%, or at least 98%, for example, over a period of one month, two months, three months, six months, or one year. In some such embodiments, the tumor is a solid tumor.

In any of the above combination therapy method embodiments, the combination of the CD80 ECD or CD80 ECD fusion molecule with an additional therapeutic agent, such as an immune stimulator, such as a PD-1/PD-L1 inhibitor, administered to the subject may inhibit tumor growth in at least one mouse syngeneic or xenograft cancer model over a period of 1 week, 10 days, 2 weeks, or 3 weeks, for example, by at least 10%, at least 20%, at least 30%, at least 40%, at least 50%, at least 60%, at least 70%, at least 80%, at least 90%, at least 95%, or at least 98%, or may inhibit growth of tumors by at least 10%, at least 20%, at least 30%, at least 40%, at least 50%, at least 60%, at least 70%, at least 80%, at least 90%, at least 95%, or at least 98% in a patient over a period of one month, two months, three months, six months, or one year. In any of the above combination therapy method embodiments, the combination of the CD80 ECD or CD80 ECD fusion molecule with an additional therapeutic agent, such as an immune stimulator, such as a PD-1/PD-L1 inhibitor, administered to the subject may reduce the volume of at least one tumor in an animal or human subject by at least 10%, at least 20%, at least 30%, at least 40%, at least 50%, at least 60%, at least 70%, at least 80%, at least 90%, at least 95%, or at least 98%, for example, over a period of one month, two months, three months, six months, or one year. In some such embodiments, the tumor is a solid tumor.

In some of the above combination therapy embodiments, the CD80 ECD or CD80 ECD fusion molecule is a CD80 ECD fusion molecule comprising 10-60 mol sialic acid (SA) to mol of CD80 ECD protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some such embodiments, the CD80 ECD fusion molecule comprises an Fc domain as fusion partner, such as a wild-type Fc domain, such as a wild-type human IgG1, IgG2, or IgG4 Fc domain. In some embodiments, the CD80 ECD fusion molecule comprises an amino acid sequence selected from SEQ ID NO: 5, SEQ ID NO: 12, SEQ ID NO:14, SEQ ID NO: 20, and SEQ ID NO: 21. In some such embodiments, the CD80 ECD or CD80 ECD fusion molecule is capable of at least 90% reduction of growth of CT26 tumor cells in mice, such as at least 95%, or at least 98%, over a period of at least ten days, such as at least two weeks, such as at least three weeks, such as over a period of ten days to two weeks or two to three weeks. In some embodiments, these results are obtained after mice are given one to three doses of 0.3 to 3 mg/kg, such as 0.3 to 0.6 mg/kg, of the CD80 ECD Fc fusion molecule.

Also comprised herein is a CD80 ECD fusion molecule comprising a human CD80 ECD polypeptide and a human IgG1 Fc domain, such as a wild-type human IgG1 Fc, wherein the CD80 ECD Fc comprises 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain comprises the amino acid sequence of SEQ ID NO:14. In some embodiments, the fusion molecule comprises the amino acid sequence of SEQ ID NO:20. In some embodiments, the molecule is capable of at least 90% reduction, such as at least 95%, or at least 98% of growth of CT26 tumor cells in mice over a period of at least ten days, such as at least two weeks, such as at least three weeks, such as over a period of ten days to two weeks or two to three weeks. In some embodiments, these results are obtained after mice are given one to three doses of 0.3 to 3 mg/kg, such as 0.3 to 0.6 mg/kg, of the CD80 ECD Fc fusion molecule.

Also comprised are compositions comprising the CD80 ECD IgG1 Fc and further comprising at least one pharmaceutically acceptable carrier. Such compositions may also contain an additional therapeutic agent. In some embodiments, the additional therapeutic agent is at least one immune stimulating agent, such as a programmed cell death 1 (PD-1)/programmed cell death ligand 1 (PD-L1) inhibitor. In some cases, the PD-1/PD-L1 inhibitor is an antibody, such as an anti-PD-1 antibody, such as nivolumab, pidilizumab, and pembrolizumab. For example, the antibody may have the heavy chain and light chain CDRs or the heavy and light chain variable regions of an antibody selected from nivolumab, pidilizumab, and pembrolizumab. In other embodiments, the PD-1/PD-L1 inhibitor is an anti-PD-L1 antibody. An anti-PD-L1 antibody may have the heavy chain and light chain CDRs of an antibody selected from BMS-936559, MPDL3280A, MEDI4736, and MSB0010718C, for example, or may comprise the heavy chain and light chain variable regions of BMS-936559, MPDL3280A, MEDI4736, or MSB0010718C. In some embodiments, the anti-PD-1 antibody is selected from BMS-936559, MPDL3280A, MEDI4736, and MSB0010718C. Alternatively, the PD-1/PD-L1 inhibitor may be a PD-1 fusion molecule such as AMP-224 or a polypeptide such as AUR-012.

This disclosure also encompasses methods of treating cancer in a subject comprising administering to the subject an effective amount of a CD80 ECD IgG1 Fc fusion molecule as described above. In some embodiments, the cancer is a solid tumor, such as a cancer selected from colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer. In some embodiments, the cancer is recurrent or progressive after a therapy selected from surgery, chemotherapy, radiation therapy, or a combination thereof.

In some of these method embodiments, the CD80 ECD Fc comprises 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21. In some embodiments, the molecule is capable of at least 90% reduction of growth of CT26 tumor cells in mice over a period of two or three weeks following inoculation of mice with tumor cells. In some embodiments, the molecule is capable of at least 95% reduction of growth of CT26 tumor cells, such as at least 98% reduction, in mice over a period of two or three weeks following inoculation of mice with tumor cells. For example, such results may be obtained when the mice are given one to three doses of 0.3 to 3.0 mg/kg, such as 0.3 to 0.6 mg/kg, of the ECD Fc fusion molecule. In some of the method embodiments, the CD80 ECD Fc comprises 10-40 mol SA to mol of CD80 ECD Fc protein, and the CD80 ECD Fc reduces growth of CT26 tumor cells in mice over a period of two or three weeks by a greater degree than a CD80 ECD Fc protein of the same amino acid sequence comprising less than 10 mol SA to mol of CD80 ECD Fc protein. The disclosure herein also comprises methods of enhancing efficacy of a CD80 ECD fusion protein in treating cancer in a subject comprising increasing the level of sialic acid (SA) in the CD80 ECD fusion protein or providing a CD80 ECD fusion protein with an increased SA level and administering the CD80 ECD fusion protein comprising an increased level of SA to the subject. In some such embodiments, the SA level is increased by 5, 10, 20, 30, 40, or 50 mol to mol of CD80 ECD protein. In some of these method embodiments, the CD80 ECD Fc comprises 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21. In some embodiments, the molecule is capable of at least 90% reduction of growth of CT26 tumor cells in mice over a period of two or three weeks. In some embodiments, the molecule is capable of at least 95%, such as at least 98%, reduction of growth of CT26 tumor cells in mice over a period of at least ten days, such as at least two weeks, such as at least three weeks, such as over a period of ten days to two weeks or two to three weeks. In some embodiments, these results are obtained after mice are given one to three doses of 0.3 to 3 mg/kg, such as 0.3 to 0.6 mg/kg, of the CD80 ECD Fc fusion molecule.

In some of these method embodiments, the enhanced efficacy is measured as an increase in overall survival, an increase in disease-free survival, or as a greater reduction in the growth of at least one tumor in an animal or human subject. In other words, one or more of these parameters is improved upon administration of the CD80 ECD fusion molecule with higher SA content compared to a CD80 ECD fusion molecule with a lower SA content. In other embodiments, the enhanced efficacy is measured as a greater reduction in tumor growth in a mouse syngeneic or xenograft model such as a CT26 mouse model or as a reduced rate of clearance in an animal or human subject. In some embodiments, the efficacy is measured as a greater reduction in tumor growth of at least one tumor in the subject or a greater reduction in tumor growth in at least one mouse syngeneic or xenograft model, and wherein the tumor growth is further reduced by at least 10%, such as at least 20%, at least 30%, at least 40%, at least 50%, at least 60%, at least 70%, at least 80%, or at least 90% upon administration of the CD80 ECD fusion molecule with increased SA level in comparison to administration of the CD80 ECD fusion molecule without the increased SA level.

It is to be understood that both the foregoing general description and the following detailed description are exemplary and explanatory only and are not restrictive of the claims. The section headings used herein are for organizational purposes only and are not to be construed as limiting the subject matter described. All references cited herein, including patent applications and publications, are incorporated herein by reference in their entireties for any purpose.

BRIEF DESCRIPTION OF THE DRAWINGS

FIG. 1a shows tumor volume at up to 21 days post-inoculation of mice with the CT26 cells. As shown in the figure, CTLA4 ECD Fc enhanced tumor growth while CD80 ECD Fc inhibited tumor growth in a statistically significant manner compared to the saline control. P-values were calculated using unpaired, two-tailed t-test analyses of the calculated tumor volumes on each day of the study (*p<0.05, p<0.01, *p<0.001). FIG. 1b shows individual tumor volumes on Day 19 post-inoculation for the three groups.

FIG. 2a shows tumor volume at up to 14 days post-inoculation. Mice administered with the CD80 ECD Fc and anti-PD-1 combination showed statistically significant reduction in tumor growth compared to either the CD80 ECD Fc (p<0.01 beginning after Day 9) or anti-PD-1 (p<0.01 on Day 14) single therapies. Statistical significance was determined via two-tailed, unpaired t-Test comparing the combination group to the CD80 ECD Fc group. FIG. 2b shows individual tumor volumes on Day 14.

FIG. 3a shows changes in tumor volume up to Day 21 post-inoculation. The mutated Fc domain resulted in enhanced anti-tumor activity, which was statistically significant beginning on Day 14 after inoculation (p<0.01). Statistical significance was determined via a two-tailed, unpaired t-Test. FIG. 3b shows individual tumor volumes on Day 21 post-inoculation.

FIG. 4a provides representative images showing CD3+ cells (top images) and corresponding DAPI staining (nuclei, bottom images) in CT26 tumors collected 7 days after injection of Saline, CD80-IgG1 WT or CD80-IgG1 MT. Both CD80-IgG1 WT and CD80-IgG1 MT increased the number of CD3+ cells within the tumors compared to vehicle but the magnitude of the increase was greater after CD80-IgG1 MT. Images were collected using the 10× objective. FIG. 4b provides representative images showing CD3+ cells (top row) and CD4+ cells (bottom row) in CT26 tumors collected 7 days after injection of Saline, CD80-IgG1 WT or CD80-IgG1 MT. The images were the taken in the same field of view but with different channels. Both CD80-IgG1 WT and CD80-IgG1 MT increased the number of infiltrating CD4+ cells compared to vehicle. The ratio of CD3+ to CD4+ cells was increased with the CD80-IgG1 MT compared to the CD80-IgG1 WT. Images were collected using the 10× objective.

FIGS. 5a and 5c show that bead-immobilized CD80-Fc alone did not cause significant T-cell activation, as measured by soluble cytokine production. FIGS. 5b and 5d show that when a small amount of OKT3-scFv (too low to cause T-cell stimulation on its own) was immobilized along with the CD80-Fc, cytokine release was observed.

DESCRIPTION OF PARTICULAR EMBODIMENTS

Definitions

Figure 1B:
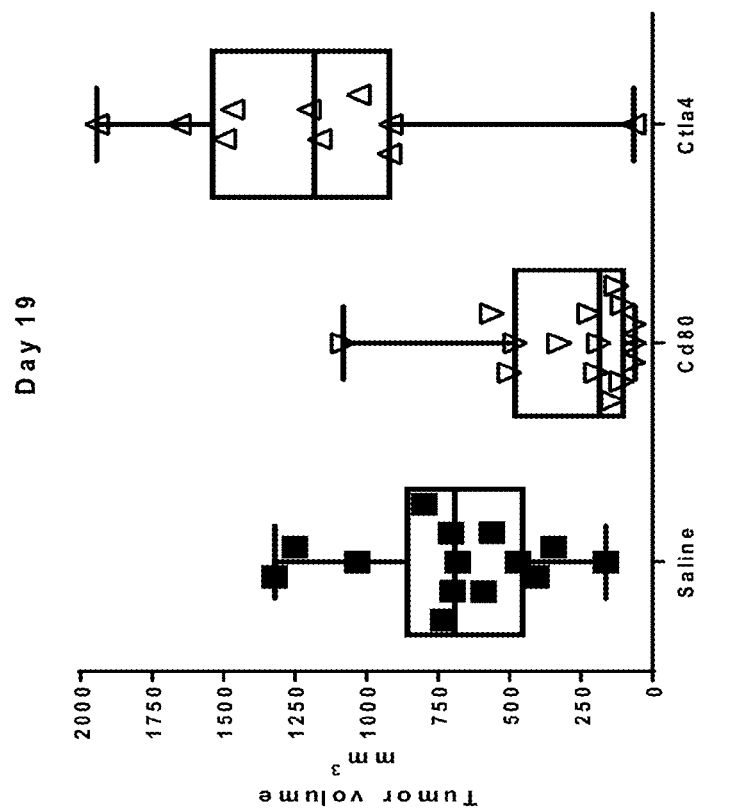
FIGS. 1a-1b show effects of administering a CD80 ECD Fc fusion molecule compared with a CTLA4 ECD Fc fusion molecule and a saline control to mice implanted with murine colorectal carcinoma cell line CT26 cells.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

Exemplary techniques used in connection with recombinant DNA, oligonucleotide synthesis, tissue culture and transformation (e.g., electroporation, lipofection), enzymatic reactions, and purification techniques are described, e.g., in Sambrook et al. *Molecular Cloning: A Laboratory Manual* (2nd ed., Cold Spring Harbor Laboratory Press, Cold Spring Harbor, N.Y. (1989)), among other places.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "CD80 extracellular domain" or "CD80 ECD" refers to an extracellular domain polypeptide of CD80, including natural and engineered variants thereof. Nonlimiting examples of CD80 ECDs include SEQ ID NOs:—. A "CD80 ECD fusion molecule" refers to a molecule comprising a CD80 ECD and a fusion partner such as an Fc domain, albumin, or PEG. The fusion partner may be covalently attached, for example, to the N- or C-terminal of the CD80 ECD or at an internal location. Nonlimiting examples of CD80 ECD fusion molecules include SEQ ID NOs:—

The terms "programmed cell death protein 1" and "PD-1" refer to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. In some embodiments, the PD-1 is a human PD-1 having the amino acid sequence of SEQ ID NO:—(precursor, with signal sequence) or SEQ ID NO:—(mature, without signal sequence).

The terms "programmed cell death 1 ligand 1" and "PD-L1" refer to one of two cell surface glycoprotein ligands for PD-1 (the other being PD-L2) that down regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank® Accession No. Q9NZQ7. In some embodiments, the PD-L1 is a human PD-L1 having the amino acid sequence of SEQ ID NO:—(precursor, with signal sequence) or SEQ ID NO:—(mature, without signal sequence).

The term "immune stimulating agent" as used herein refers to a molecule that stimulates the immune system by either acting as an agonist of an immune-stimulatory molecule, including a co-stimulatory molecule, or acting as an antagonist of an immune inhibitory molecule, including a co-inhibitory molecule. An immune stimulating agent may be a biologic, such as an antibody or antibody fragment, other protein, or vaccine, or may be a small molecule drug. An "immune stimulatory molecule" includes a receptor or ligand that acts to enhance, stimulate, induce, or otherwise "turn-on" an immune response. Immune stimulatory molecules as defined herein include co-stimulatory molecules. An "immune inhibitory molecule" includes a receptor or ligand that acts to reduce, inhibit, suppress, or otherwise "turn-off" an immune response. Immune inhibitory molecules as defined herein include co-inhibitory molecules. Such immune stimulatory and immune inhibitory molecules may be, for example, receptors or ligands found on immune cells such as a T cells, or found on cells involved in innate immunity such as NK cells.

The term "PD-1/PD-L1 inhibitor" refers to a moiety that disrupts the PD-1/PD-L1 signaling pathway. In some embodiments, the inhibitor inhibits the PD-1/PD-L1 signaling pathway by binding to PD-1 and/or PD-L1. In some embodiments, the inhibitor also binds to PD-L2. In some embodiments, a PD-1/PD-L1 inhibitor blocks binding of PD-1 to PD-L1 and/or PD-L2. Nonlimiting exemplary PD-1/PD-L1 inhibitors include antibodies that bind to PD-1; antibodies that bind to PD-L1; fusion proteins, such as AMP-224; and peptides, such as AUR-012.

The term "antibody that inhibits PD-1" refers to an antibody that binds to PD-1 or binds to PD-L1 and thereby inhibits PD-1 and/or PD-L1 signaling. In some embodiments, an antibody that inhibits PD-1 binds to PD-1 and blocks binding of PD-L1 and/or PD-L2 to PD-1. In some embodiments, an antibody that inhibits PD-1 binds to PD-L1 and blocks binding of PD-1 to PD-L1. An antibody that inhibits PD-1 that binds to PD-L1 may be referred to as an anti-PD-L1 antibody. An antibody that inhibits PD-1 that binds to PD-1 may be referred to as an anti-PD-1 antibody.

With reference to CD80 ECDs and CD80 ECD fusion molecules, the term "blocks binding of" a ligand, and grammatical variants thereof, refers to the ability to inhibit an interaction between CD80 and a CD80 ligand, such as CD28, CTLA4, or PD-L1. Such inhibition may occur through any mechanism, including by the CD80 ECDs or CD80 ECD fusion molecules competing for binding with CD80 ligands.

With reference to anti-PD-1 antibodies and PD-1 fusion molecules or peptides the term "blocks binding of" a ligand, such as PD-L1, and grammatical variants thereof, are used to refer to the ability to inhibit the interaction between PD-1 and a PD-1 ligand, such as PD-L1. Such inhibition may occur through any mechanism, including direct interference with ligand binding, e.g., because of overlapping binding sites on PD-1, and/or conformational changes in PD-1 induced by the antibody that alter ligand affinity, etc., or, in the case of a PD-1 fusion molecule or peptide, by competing for binding with a PD-1 ligand.

"Affinity" or "binding affinity" refers to the strength of the sum total of noncovalent interactions between a single binding site of a molecule (e.g., a polypeptide) and its binding partner (e.g., a ligand). In some embodiments, "binding affinity" refers to intrinsic binding affinity, which reflects a 1:1 interaction between members of a binding pair (e.g., polypeptide and ligand). The affinity of a molecule X for its partner Y can generally be represented by the dissociation constant ($K_d$).

The term "antibody" as used herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

The term "heavy chain variable region" refers to a region comprising heavy chain HVR1, framework (FR) 2, HVR2, FR3, and HVR3. In some embodiments, a heavy chain variable region also comprises at least a portion of an FR1 and/or at least a portion of an FR4.

The term "heavy chain constant region" refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain variable region" refers to a region comprising light chain HVR1, framework (FR) 2, HVR2, FR3, and HVR3. In some embodiments, a light chain variable region also comprises an FR1 and/or an FR4.

The term "light chain constant region" refers to a region comprising a light chain constant domain, $C_L$. Nonlimiting exemplary light chain constant regions include λ and κ.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" refers to each of the regions of an antibody variable domain which are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" ("CDRs"), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The terms hypervariable regions (HVRs) and complementarity determining regions (CDRs) both refer to portions of the variable region that form the antigen binding regions.

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "reduce" or "reduces" when applied to a parameter such as tumor volume means to lower the level of that parameter in an observable, measurable way. In some embodiments, the reduction may be by at least 10%, such as by at least 20%, at least 30%, at least 40%, or at least 50%. In some embodiments, the reduction may be statistically significant compared to an alternative treatment or control.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The terms "resistant" or "nonresponsive" when used in the context of treatment with a therapeutic agent, means that the subject shows decreased response or lack of response to a standard dose of the therapeutic agent, relative to the subject's response to the standard dose of the therapeutic agent in the past, or relative to the expected response of a similar subject with a similar disorder to the standard dose of the therapeutic agent. Thus, in some embodiments, a subject may be resistant to therapeutic agent although the subject has not previously been given the therapeutic agent, or the subject may develop resistance to the therapeutic agent after having responded to the agent on one or more previous occasions.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "tissue sample" refers to a collection of similar cells obtained from a tissue of a subject. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, synovial fluid, or interstitial fluid; cells from any time in gestation or development of the subject. In some embodiments, a tissue sample is a synovial biopsy tissue sample and/or a synovial fluid sample. In some embodiments, a tissue sample is a synovial fluid sample. The tissue sample may also be primary or cultured cells or cell lines. Optionally, the tissue sample is obtained from a disease tissue/organ. The tissue sample may contain compounds that are not naturally intermixed with the tissue in nature such as preservatives, anticoagulants, buffers, fixatives, nutrients, antibiotics, or the like. A "control sample" or "control tissue", as used herein, refers to a sample, cell, or tissue obtained from a source known, or believed, not to be afflicted with the disease for which the subject is being treated.

For the purposes herein a "section" of a tissue sample means a part or piece of a tissue sample, such as a thin slice of tissue or cells cut from a solid tissue sample.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells (i.e. "solid tumors") or may be leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

"Treatment," as used herein, refers to both therapeutic treatment and prophylactic or preventative measures, wherein the object is to prevent or slow down (lessen) the targeted pathologic condition or disorder. In certain embodiments, the term "treatment" covers any administration or application of a therapeutic for disease in a mammal, including a human, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those prone to have the disorder or those in whom the disorder is to be prevented.

The term "efficacy" as used herein may be determined from one or more parameters such as survival or disease-free survival over a period of time such as 1 year, 5 years, or 10 years, as well as parameters such as the reduction in growth of one or more tumors in a subject. Pharmacokinetic parameters such as bioavailability and underlying parameters such as clearance rate may also impact efficacy. Thus, an "enhanced efficacy" (i.e. an improvement in efficacy) may be due to improved pharmacokinetic parameters as well as improved potency, and may be measured by comparing clearance rates and tumor growth in test animals or in human subjects, as well as parameters such as survival, rate of recurrence, or disease-free survival.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of a CD80 ECD or CD80 ECD fusion molecule may vary according to factors such as the disease state, age, sex, and weight of the individual, and the ability of the drug to elicit a desired response in the individual. A therapeutically effective amount encompasses an amount in which any toxic or detrimental effects of the drug are outweighed by the therapeutically beneficial effects. In some embodiments, the expression "effective amount" refers to an amount of the drug that is effective for treating the cancer.

Administration "in combination with" one or more further therapeutic agents, such as an immune stimulating agent, includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Exemplary CD80 Extracellular Domain and Extracellular Domain Fusion Molecules

CD80 ECD and CD80 ECD fusion molecules are provided herein. CD80 ECDs, for example, may comprise the ECDs of human CD80 isoform 1, isoform 2, and isoform 3 (see SEQ ID NOs: 1-3. In some embodiments, CD80 ECDs and may comprise the amino acid sequence of SEQ ID NO:5.

CD80 ECD fusion molecules may comprise fusion partners such as polymers, polypeptides, lipophilic moieties, and succinyl groups. Exemplary polypeptide fusion partners include, but are not limited to, serum albumin and an IgG Fc domain. Further exemplary polymer fusion partners include, but are not limited to, polyethylene glycol, including polyethylene glycols having branched and/or linear chains. The amino acid sequences of certain exemplary Fc domains are shown in SEQ ID NOs: 9-16 herein.

In certain embodiments, the CD80 ECD or CD80 ECD fusion molecule lacks a signal peptide. In certain embodiments, the CD80 ECD or CD80 ECD fusion molecule includes at least one signal peptide, which may be selected from a native CD80 signal peptide (SEQ ID NO: 7 or amino acids 1-34 of SEQ ID NO:1) and/or a heterologous signal peptide.

In the case of a CD80 ECD fusion molecule, the fusion partner may be linked to either the amino-terminus or the carboxy-terminus of the polypeptide. In certain embodiments, the polypeptide and the fusion partner are covalently linked. If the fusion partner is also a polypeptide ("the fusion partner polypeptide"), the polypeptide and the fusion partner polypeptide may be part of a continuous amino acid sequence. In such cases, the polypeptide and the fusion partner polypeptide may be translated as a single polypeptide from a coding sequence that encodes both the polypeptide and the fusion partner polypeptide. In some such cases, the two polypeptides are directly linked in sequence such that the N-terminal of one polypeptide immediately follows the C-terminal of the other with no intervening amino acids. In other cases, a linker peptide sequence is inserted in between the two polypeptides, such as a GS linker sequence. In certain embodiments, a CD80 ECD and the fusion partner are covalently linked through other means, such as, for example, a chemical linkage other than a peptide bond. In certain embodiments, the polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

In some embodiments, the CD80 ECD fusion molecule comprises the sequence of SEQ ID NO: 20 or 21.

CD80 ECD fusion molecules may, depending on how they are produced, have different levels of particular glycosylation modifications. For example, a CD80 ECD fusion molecule may have different concentrations of sialic acid residues in relation to the concentration of the CD80 ECD protein. In some embodiments, a higher sialic acid content may have a longer clearance time in the body and thus an increased overall bioavailability. In some embodiments, the sialic acid content of the CD80 ECD fusion molecule is from 10 to 60 mol sialic acid (SA) to mol protein. In some embodiments, the sialic acid content of the CD80 ECD fusion molecule is from 15 to 60 mol sialic acid (SA) to mol protein. For example, in some embodiments, the SA content is 10-40 mol SA/mol protein, such as 15-30 mol SA/mol protein, such as 15-25 mol SA/mol protein, such as 20-40 mol SA/mol protein, such as 20-30 mol SA/mol protein, such as 30-40 mol SA/mol protein, such as 10, 15, 20, 25, 30, 35, or 40 mol SA/mol protein. In some embodiments, the SA content is at least 15 mol SA/mol protein, such as at least 20 mol SA/mol protein, at least 25 mol SA/mol protein, at least 30 mol SA/mol protein, at least 35 mol SA/mol protein, or at least 40 mol SA/mol protein. In some such embodiments, the fusion partner is an Fc domain, such as a human IgG1, IgG2, or IgG4 Fc domain.

In some embodiments, the SA content of the CD80 ECD fusion molecule is increased or is maintained at a relatively high level in comparison to current CD80 ECD fusion molecules. In some embodiments, an increase in SA content, such as by 5, 10, 15, 20, 30, 40 or 50 mol SA to mol of CD80 ECD protein, may lead to an enhanced efficacy in at least one mouse syngeneic or xenograft tumor model. For example, in some embodiments, tumor growth in a mouse tumor model may be further reduced by at least 5%, 10%, 20%, 30%, 40% 50%, 60%, 70%, 80%, 90%, 95%, or 98% when there is an increase in SA content, such as by 5, 10, 15, 20, 30, 40 or 50 mol SA to mol of CD80 ECD protein.

For example, in some embodiments, a CD80 ECD Fc fusion molecule, such as a fusion molecule comprising a human IgG1 Fc domain comprising between 10 and 60 mol SA/mol protein is capable of at least 80%, such as at least 90%, such as at least 95%, such as at least 98% tumor cell growth inhibition in at least one mouse syngeneic or xenograft cancer model over a period of at least ten days or at least two weeks or at least three weeks, such as ten days to two weeks or two to three weeks following inoculation with tumor cells. In some such embodiments, the molecule comprises at least 15 mol SA/mol protein, such as at least 20 mol SA/mol protein, or a range from 15-30, 15-25, or 20-30 mol SA/mol protein. In some embodiments, the mouse model is a CT26, MC38, or B16 mouse tumor model. In some embodiments, the mice are given one to three doses of the molecule at 0.3 to 3.0 mg/kg, such as at 0.3 to 0.6 mg/kg, for example over a period of one week, once tumors have reached a minimum volume. In some embodiments, the Fc domain comprises the amino acid sequence of SEQ ID NO:14. In some embodiments, the CD80 ECD fusion molecule comprises the sequence of SEQ ID NO: 20 or 21.

In some embodiments, the CD80 ECD Fc fusion molecule reduces growth of CT26 tumor cells in mice over a period of at least ten days or at least two weeks or at least three weeks, such as ten days to two weeks or two to three weeks, after inoculation by a greater degree than a CD80 ECD Fc fusion protein with the identical amino acid sequence but a lower level of SA per mol of protein. In some embodiments, the CD80 ECD Fc fusion molecule reduces growth of CT26 tumors in mice over a period of at least ten days or at least two weeks, such as over ten days to two weeks or two to three weeks, after inoculation by a greater degree than an anti-CTLA4 antibody, such as anti-CTLA4 antibody clone 9D9. In some such embodiments, the CD80 ECD Fc molecule is dosed one to three times at 0.3 mg/kg, 0.6 mg/kg, or 3.0 mg/kg while the anti-CTLA4 antibody is dosed the same number of times at 1.5 or 10 mg/kg. In some such embodiments, the model is a CT26, MC38, or B16 murine tumor model.

Example 6 herein, for example, provides data showing that treatment of a mouse syngeneic tumor model with a CD80 ECD fusion molecule having 15 or 20 mol SA/mol protein resulted in at least 93% inhibition of tumor growth after one dose of 0.3 mg/kg, whereas the same treatment with a molecule having only 5 mol SA/mol protein did not significantly inhibit tumor growth. Similarly, a 0.6 mg/kg dose of the CD80 ECD fusion molecule having 15 or 20 mol SA/mol protein resulted in 95% to 98% inhibition of tumor growth, whereas the same treatment with the molecule with 5 mol SA/mol protein inhibited tumor growth by only 70%. (See FIG. 6.) The degree of inhibition was assessed about three weeks following inoculation with the tumors.

Figure 7:
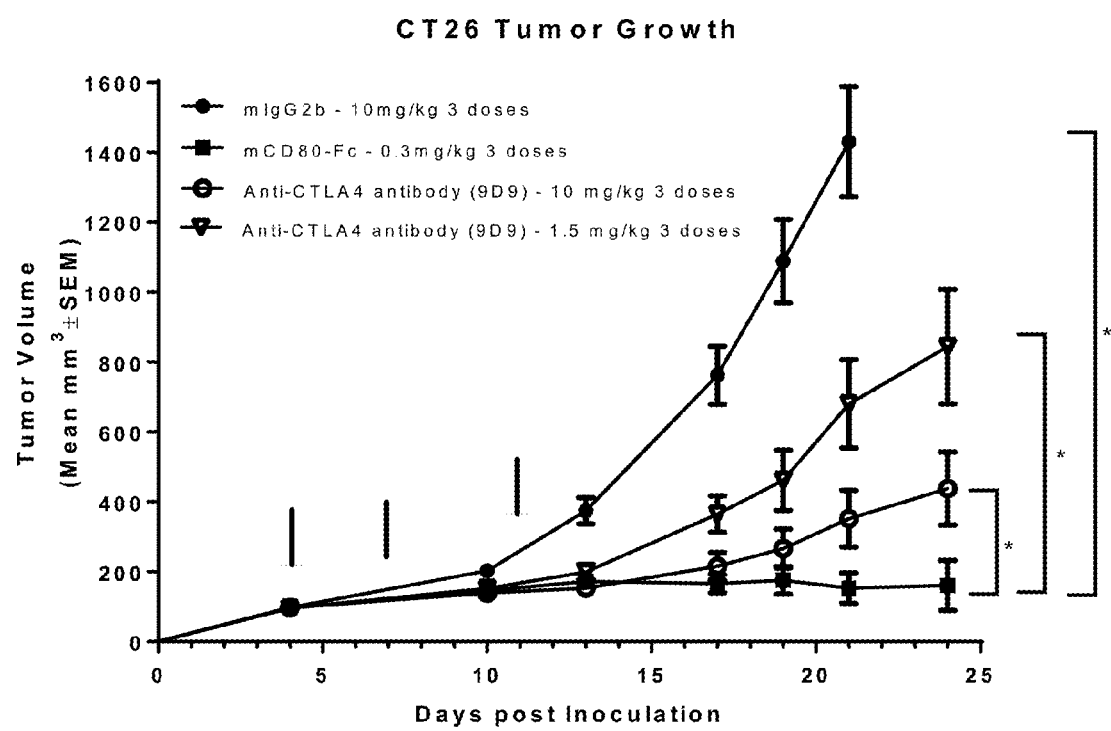
FIG. 7 shows tumor growth of CT26 tumors treated with mouse IgG2b at 10 mg/kg; murine CD80 ECD-Fc SA 20 mol/mol at 0.3 mg/kg; anti-CTLA4 antibody clone 9D9 at 10 mg/kg; and anti-CTLA4 antibody clone 9D9 at 1.5 mg/kg. Arrows indicate when mice were dosed. The asterisk symbol (*) denotes statistically significant differences between murine CD80 ECD-Fc SA 20 mol/mol at 0.3 mg/kg and the other treatments.
Figure 8:
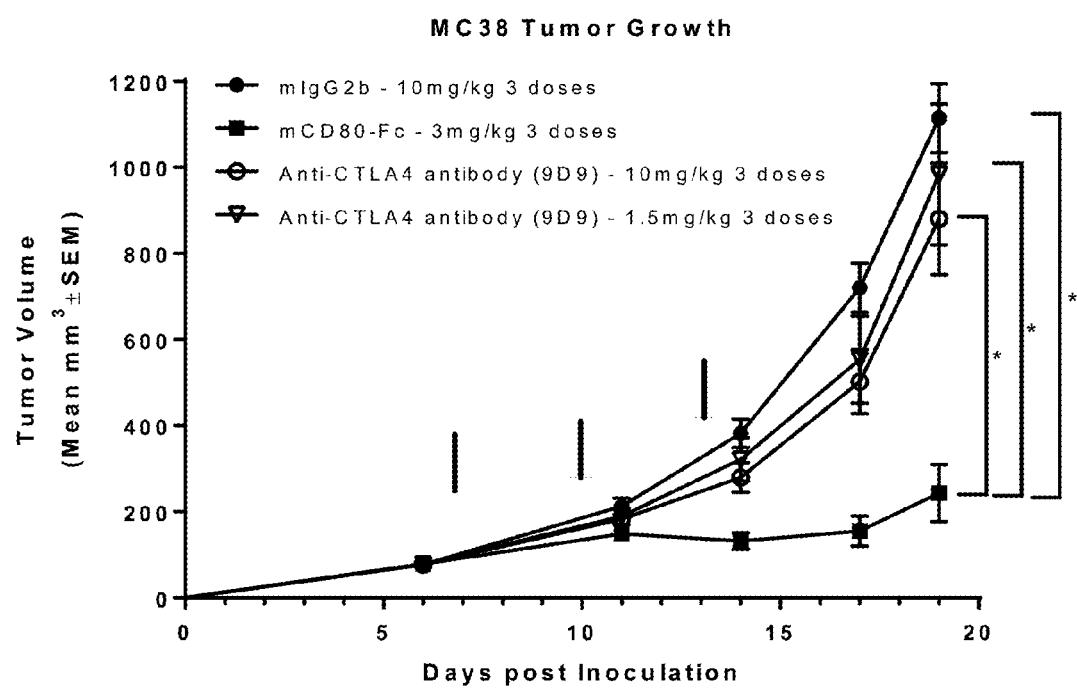
FIG. 8 shows tumor growth of MC38 tumors treated with mouse IgG2b at 10 mg/kg; murine CD80 ECD-Fc SA 20 mol/mol at 3 mg/kg; anti-CTLA4 antibody clone 9D9 at 10 mg/kg; and anti-CTLA4 antibody clone 9D9 at 1.5 mg/kg. Arrows indicate when mice were dosed. The asterisk symbol (*) denotes statistically significant differences between murine CD80 ECD-Fc SA 20 mol/mol at 3 mg/kg and the other treatments.
Figure 9:
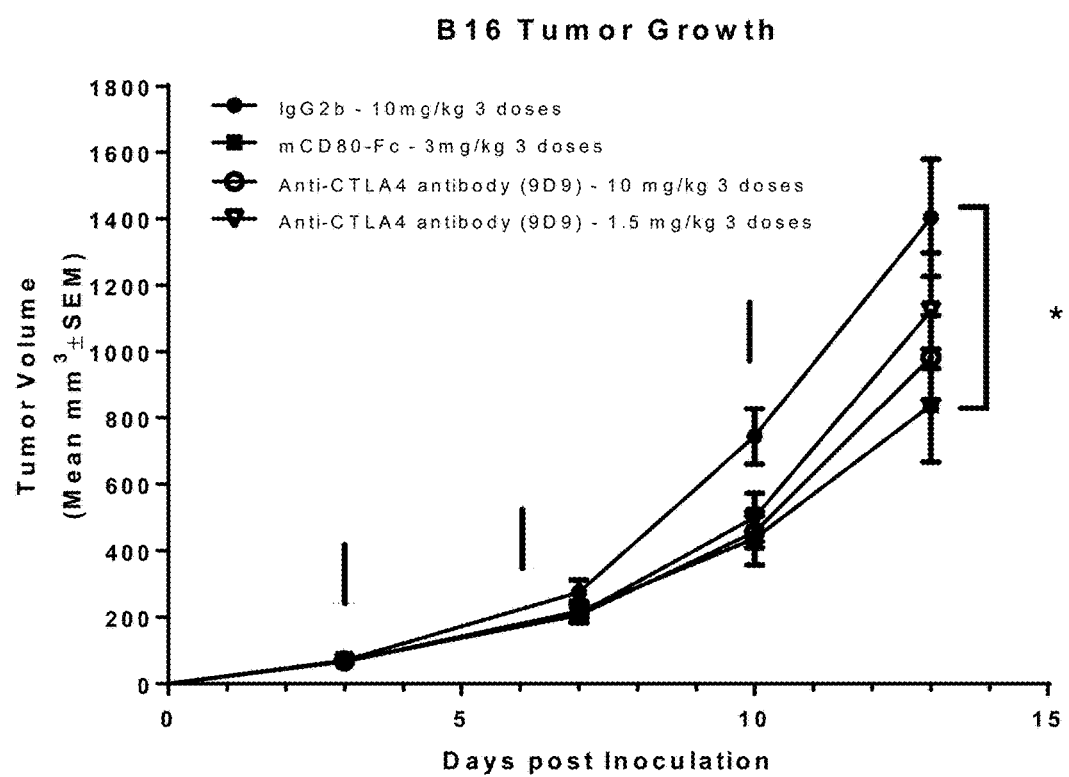
FIG. 9 shows tumor growth of B16 tumors treated with mouse IgG2b at 10 mg/kg; murine CD80 ECD-Fc SA 20 mol/mol at 3 mg/kg; anti-CTLA4 antibody clone 9D9 at 10 mg/kg; and anti-CTLA4 antibody clone 9D9 at 1.5 mg/kg. Arrows indicate when mice were dosed. The asterisk symbol (*) denotes statistically significant differences between murine CD80 ECD-Fc SA 20 mol/mol at 3 mg/kg and the other treatments.

Further, Example 7 herein shows data on a CD80 ECD Fc fusion molecule (a mouse surrogate) having 20 mol SA/mol protein in three different syngeneic mouse tumor models, the CT26, MC38, and B16 models at 0.3 mg/kg (CT26) or 3.0 mg/kg (MC38 and B16) doses compared to an anti-CTLA4 antibody (clone 9D9) at 1.5 mg/kg and 10 mg/kg doses. Each protein was dosed three times over a 7-day period a few days after inoculation with tumor cells, as depicted in FIGS. 7-9 (the arrows showing the days of dosing). In each case, the CD80 ECD Fc was superior in tumor growth inhibition to the anti-CTLA4 antibody over the course of the two to three week study. (FIGS. 7-9.) For example, in the CT26 model at day 21 after inoculation with tumor cells, the CD80 ECD Fc fusion molecule showed a 90% reduction in tumor growth compared to 75% or 53% for the two dose levels of anti-CTLA4. In the MC38 model at day 19 after inoculation, the CD80 ECD Fc molecule showed about 80% reduction in tumor growth inhibition compared to only 21% tumor growth for the higher dose of anti-CTLA4 and no tumor growth inhibition for the lower anti-CTLA4 dose. In the B16 model, the CD80 ECD Fc fusion molecule showed 41% tumor growth inhibition on day 13 after inoculation while the anti-CTLA4 antibody did not inhibit tumor growth at either dose level. (See FIGS. 7-9.)

Based on these studies, a CD80 ECD fusion molecule may be capable of a certain percentage of tumor growth inhibition over at least a two week period of time, for example, when about two weeks after the mice have been inoculated with the tumor cells, and also following dosing with the fusion molecule, an average tumor growth inhibition at about the stated percentage is observed in the treated mice. A CD80 ECD fusion molecule may be capable of a certain percentage of tumor growth inhibition over a two to three week period of time, for example, when between two and three weeks after the mice have been inoculated with the tumor cells, and also following dosing with the fusion molecule, an average tumor growth inhibition at about the stated percentage is observed in the treated mice.

Examples 6 and 7 also show that many mice from the CT26 model treated with CD80 ECD fusion molecule had a complete tumor regression over these two to three week time periods. Moreover, a larger percentage of mice had complete tumor regression with CD80 ECD fusion molecule with higher SA content than with the comparison treatments and a larger percentage of mice had complete tumor regression with CD80 ECD fusion molecule than with an anti-CTLA4 antibody. Thus, in some embodiments, treatment CD80 ECD fusion molecule, such as with 0.3 mg/kg to 0.6 mg/kg CD80 ECD fusion molecule or with 0.3 mg/kg to 3.0 mg/kg CD80 ECD fusion molecule, may result in complete tumor regression in mice in a syngeneic or xenograft model such as CT26, MC38, or B16.

Exemplary Fc Domain Fusion Partners

In some embodiments, the CD80 ECD fusion molecule has an Fc domain as fusion partner. In some embodiments, the Fc domain is derived from human IgG1, IgG2, IgG3, or IgG4. In some embodiments, the Fc domain has a wild-type sequence, such as a wild-type human IgG1 or IgG2 (e.g. IgG2a) sequence. In other embodiments, the Fc domain is either a natural or engineered variant. In some embodiments, an Fc domain is chosen that has altered interactions of the Fc with one or more Fc gamma receptors. In some embodiments, an Fc domain is chosen that has altered interactions of the Fc with one or more complement factors. In some embodiments, an Fc domain is chosen that has altered interactions of the Fc with one or more Fc gamma receptors and that has altered interactions with one or more complement factors.

In some embodiments, the Fc domain comprises at least one point mutation as described in WO 2014/144960. In some embodiments, the Fc domain is a human Fc domain with a substitution at one or more of positions E233, L234, L235, P238, D265, N297, A327, P329, or P331 (wherein the numbering of these positions is according to the EU index as in Kabat). In some embodiments, the Fc domain is a human Fc domain with a mutation at L234, L235, and/or P331. In some embodiments, the Fc domain is a human Fc domain with the substitutions L234F, L235E, and P331S. (See, e.g., SEQ ID NO:12.) In some embodiments, the Fc domain has an amino acid substitution at position N297. (See, e.g., SEQ ID NO: 13.) In some embodiments, the Fc domain comprises a C237S mutation. (See, e.g., SEQ ID NO: 9.)

In some embodiments, a mutated Fc fusion partner causes the CD80 ECD Fc fusion molecule to have altered interactions with one or more Fc gamma receptors compared to those of a CD80 ECD fusion molecule with the same amino acid sequence except for the Fc domain mutations. In some embodiment, the Fc has reduced affinity for Fc gamma receptors such as one or more of FcRN, RI, RIIA, RIIB, and RIII compared to a wild-type Fc domain. In some embodiments, the Fc has reduced affinity for all of FcRN, RI, RIIA, RIIB, and RIII compared to a wild-type Fc domain.

In some embodiments, a mutated Fc fusion partner causes the CD80 ECD Fc fusion molecule to have altered interactions with at one or more complement factors such as C1, C2, C3, C4, and their cleavage products, such as C4a, C4b, C2a, C2b, C3a, and C3b. In some embodiments, a mutated Fc fusion partner causes the CD80 ECD Fc fusion molecule to have altered interactions with one or more complement factors compared to those of a CD80 ECD fusion molecule with the same amino acid sequence except for the Fc domain mutations.

In some embodiments the CD80 ECD and the fusion partner, such as an Fc fusion partner, are directly linked such that the N- or C-terminal amino acid of the Fc immediately precedes or follows the N- or C-terminal amino acid of the CD80 ECD sequence. (See, e.g., SEQ ID NOs: 20 and 21.) In other embodiments, the CD80 ECD and fusion partner are joined by a linker molecule, such as by a linker peptide sequence, such as by a GS linker sequence.

Therapeutic Compositions and Methods

Methods of Treating Cancer

In some embodiments, methods for treating cancer are provided, comprising administering an effective amount of a CD80 ECD or CD80 ECD fusion molecule.

In some embodiments, the cancer may be benign (also referred to as a benign tumor), pre-malignant, or malignant. In some embodiments, the cancer may comprise solid cancer cells (i.e. "solid tumors") or alternatively, it may comprise leukemic cancer cells. In some embodiments, the CD80 ECD or CD80 ECD fusion molecule is effective to reduce cancer growth in a human or animal subject, or in a mouse syngeneic or xenograft model for the cancer being treated. In some embodiments, the CD80 ECD or CD80 ECD fusion molecule is effective to reduce tumor volume, such as in a mouse syngeneic or xenograft model for the cancer being treated.

Examples of particular cancers that may be treated include but are not limited to, carcinoma, lymphoma, blastoma, sarcoma, and leukemia. More particular nonlimiting examples of such cancers include but are not limited to squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

In any of the above method embodiments, the CD80 ECD or CD80 ECD fusion molecule administered to the subject may inhibit tumor growth in a mouse syngeneic xenograft cancer model over a period of 1 week, 10 days, 2 weeks, or 3 weeks, for example, by at least 10%, at least 20%, at least 30%, at least 40%, at least 50%, at least 60%, at least 70%, at least 80%, at least 90%, at least 95%, or at least 98%. In some embodiments, the CD80 ECD fusion molecule may inhibit tumor growth in a CT26 mouse xenograft tumor model by at least 10%, at least 20%, at least 30%, at least 40%, at least 50%, at least 60%, at least 70%, at least 80%, at least 90%, at least 95%, or at least 98% at two weeks or at three weeks post-inoculation. In some such cases, the fusion molecule may be dosed one to three times at 0.3 to 3 mg/kg, such as at 0.3 to 0.6 mg/kg. In any of the above method embodiments, administration of the CD80 ECD or CD80 ECD fusion molecule administered to the subject may reduce the volume of at least one tumor in a human or animal subject by at least 10%, at least 20%, at least 30%, at least 40%, at least 50%, at least 60%, at least 70%, at least 80%, at least 90%, at least 95%, or at least 98%, for example, over a period of one month, two months, three months, six months, or one year. In some cases, the CD80 ECD Fc fusion molecule may be capable of resulting in complete tumor regression in a mouse tumor model such as a CT26 model, for example in a significant portion of tested mice, such as at least 40%, or at least 50% of mice.

In any of these methods, the CD80 ECD or CD80 ECD fusion molecule may be a CD80 ECD Fc comprising 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21.

Combination Treatments with Immune Stimulating Agents Including PD-1/PD-L1 Inhibitors In some embodiments, the CD80 ECD or CD80 ECD fusion molecule is administered to treat one of the above cancers in combination with an effective amount of at least one immune stimulating agent. Immune stimulating agents may include, for example, a small molecule drug or a biologic. Examples of biologic immune stimulating agents include, but are not limited to, antibodies, antibody fragments, fragments of receptor or ligand polypeptides, for example that block receptor-ligand binding, vaccines and cytokines.

In some embodiments, the at least one immune stimulating agent comprises an agonist of an immune stimulatory molecule, including a co-stimulatory molecule, while in some embodiments, the at least one immune stimulating agent comprises an antagonist of an immune inhibitory molecule, including a co-inhibitory molecule. In some embodiments, the at least one immune stimulating agent comprises an agonist of an immune-stimulatory molecule, including a co-stimulatory molecule, found on immune cells, such as T cells. In some embodiments, the at least one immune stimulating agent comprises an antagonist of an immune inhibitory molecule, including a co-inhibitory molecule, found on immune cells, such as T cells. In some embodiments, the at least one immune stimulating agent comprises an agonist of an immune stimulatory molecule, including a co-stimulatory molecule, found on cells involved in innate immunity, such as NK cells. In some embodiments, the at least one immune stimulating agent comprises an antagonist of an immune inhibitory molecule, including a co-inhibitory molecule, found on cells involved in innate immunity, such as NK cells. In some embodiments, the combination enhances the antigen-specific T cell response in the treated subject and/or enhances the innate immunity response in the subject. In some embodiments, the combination results in an improved anti-tumor response in an animal cancer model, such as a syngeneic or xenograft model, compared to administration of either the CD80 ECD or CD80 ECD fusion molecule or immune stimulating agent alone. In some embodiments, the combination results in a synergistic response in an animal cancer model, such as a syngeneic or xenograft model, compared to administration of either the CD80 ECD or CD80 ECD fusion molecule or immune stimulating agent alone.

In any of the above combination therapy method embodiments, the combination of the CD80 ECD or CD80 ECD fusion molecule with the immune stimulating agent, such as a PD-1/PD-L1 inhibitor, that is administered to the subject may inhibit tumor growth in a mouse syngeneic or xenograft cancer model over a period of 1 week, 10 days, 2 weeks, or 3 weeks, for example, by at least 10%, at least 20%, at least 30%, at least 40%, at least 50%, at least 60%, at least 70%, at least 80%, at least 90%, at least 95%, or at least 98%. In any of the above combination therapy method embodiments, the combination of the CD80 ECD or CD80 ECD fusion molecule with the immune stimulating agent, such as a PD-1/PD-L1 inhibitor, that is administered to the subject may reduce the volume of at least one tumor in the subject or in an animal model by at least 10%, at least 20%, at least 30%, at least 40%, at least 50%, at least 60%, at least 70%, at least 80%, at least 90%, or at least 95%, for example, over a period of one month, two months, three months, six months, or one year.

In any of the combination therapy methods, the CD80 ECD or CD80 ECD fusion molecule may be a CD80 ECD Fc comprising 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21.

In certain embodiments, an immune stimulating agent targets a stimulatory or inhibitory molecule that is a member of the immunoglobulin super family (IgSF). For example, an immune stimulating agent may be an agent that targets (or binds specifically to) another member of the B7 family of polypeptides. An immune stimulating agent may be an agent that targets a member of the TNF family of membrane bound ligands or a co-stimulatory or co-inhibitory receptor binding specifically to a member of the TNF family. Exemplary TNF and TNFR family members that may be targeted by immune stimulating agents include CD40 and CD40L, OX-40, OX-40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY and NGFR.

In some embodiments, an immune stimulating agent may comprise (i) an antagonist of a protein that inhibits T cell activation (e.g., immune checkpoint inhibitor) such as CTLA4, LAG-3, TIM3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, TIM-4, and ILT4 and/or may comprise (ii) an agonist of a protein that stimulates T cell activation such as B7-2, CD28, 4-1BB (CD137), 4-1BBL, ICOS, ICOS-L, OX40, OX40L, GITR, GITRL, CD70, CD27, CD40, CD40L, DR3 and CD28H.

In some embodiments, an immune stimulating agent may comprise an agent that inhibits or is an antagonist of a cytokine that inhibits T cell activation (e.g., IL-6, IL-10, TGF-β, VEGF, and other immunosuppressive cytokines), and it some embodiments an immune stimulating agent may comprise an agent that is an agonist of a cytokine, such as IL-2, IL-7, IL-12, IL-15, IL-21 and IFNα (e.g., the cytokine itself) that stimulates T cell activation. In some embodiments, immune stimulating agents may comprise an antagonist of a chemokine, such as CXCR2 (e.g., MK-7123), CXCR4 (e.g. AMD3100), CCR2, or CCR4 (mogamulizumab).

In some embodiments, immune stimulating agents may include antagonists of inhibitory receptors on NK cells or agonists of activating receptors on NK cells. For example, a CD80 ECD or CD80 ECD fusion molecule can be combined with an antagonist of KIR.

Immune stimulating agents may also include agents that inhibit TGF-β signaling, agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Immune stimulating agents may also include certain vaccines such as mesothelin-targeting vaccines or attenuated *listeria* cancer vaccines, such as CRS-207.

Immune stimulating agents may also comprise agents that deplete or block Treg cells, such as agents that specifically bind to CD25.

Immune stimulating agents may also comprise agents that inhibit a metabolic enzyme such as indoleamine dioxigenase (IDO), dioxigenase, arginase, or nitric oxide synthetase.

Immune stimulating agents may also comprise agents that inhibit the formation of adenosine or inhibit the adenosine A2A receptor.

Immune stimulating agents may also comprise agents that reverse/prevent T cell anergy or exhaustion and agents that trigger an innate immune activation and/or inflammation at a tumor site.

In some embodiments, immune stimulating agents may comprise a CD40 agonist such as a CD40 agonist antibody. The CD80 ECD or CD80 ECD fusion molecule may also be combined with a combinatorial approach that targets multiple elements of the immune pathway, such as one or more of the following: at least one agent that enhances tumor antigen presentation (e.g., dendritic cell vaccine, GM-CSF secreting cellular vaccines, CpG oligonucleotides, imiquimod); at least one agent that inhibits negative immune regulation e.g., by inhibiting CTLA4 pathway and/or depleting or blocking Treg or other immune suppressing cells; a therapy that stimulates positive immune regulation, e.g., with agonists that stimulate the CD-137, OX-40 and/or GITR pathway and/or stimulate T cell effector function; at least one agent that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; at least one agent that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); at least one agent that inhibits a metabolic enzyme such as indoleamine dioxigenase (IDO), dioxigenase, arginase or nitric oxide synthetase; at least one agent that reverses/prevents T cell anergy or exhaustion; a therapy that triggers an innate immune activation and/or inflammation at a tumor site; administration of immune stimulatory cytokines or blocking of immuno repressive cytokines.

For example, a CD80 ECD or CD80 ECD fusion molecule can be used with one or more agonistic agents that ligate positive costimulatory receptors; one or more antagonists (blocking agents) that attenuate signaling through inhibitory receptors, such as antagonists that overcome distinct immune suppressive pathways within the tumor microenvironment; one or more agents that increase systemically the frequency of anti-tumor immune cells, such as T cells, deplete or inhibit Tregs (e.g., by inhibiting CD25); one or more agents that inhibit metabolic enzymes such as IDO; one or more agents that reverse/prevent T cell anergy or exhaustion; and one or more agents that trigger innate immune activation and/or inflammation at tumor sites.

In one embodiment, the at least one immune stimulating agent comprises a CTLA4 antagonist, such as an antagonistic CTLA4 antibody. Suitable CTLA4 antibodies include, for example, YERVOY (ipilimumab) or tremelimumab.

In some embodiments, the at least one immune stimulating agent comprises a LAG-3 antagonist, such as an antagonistic LAG-3 antibody. Suitable LAG-3 antibodies include, for example, BMS-986016 (WO10/19570, WO14/08218), or IMP-731 or IMP-321 (WO08/132601, WO09/44273).

In some embodiments, the at least one immune stimulating agent comprises a CD137 (4-1BB) agonist, such as an agonistic CD137 antibody. Suitable CD137 antibodies include, for example, urelumab or PF-05082566 (WO12/32433).

In some embodiments, the at least one immune stimulating agent comprises a GITR agonist, such as an agonistic GITR antibody. Suitable GITR antibodies include, for example, TRX-518 (WO06/105021, WO09/009116), MK-4166 (WO11/028683) or a GITR antibody disclosed in WO2015/031667.

In some embodiments, the at least one immune stimulating agent comprises an OX40 agonist, such as an agonistic OX40 antibody. Suitable OX40 antibodies include, for example, MEDI-6383, MEDI-6469 or MOXR0916 (RG7888; WO06/029879).

In some embodiments, the at least one immune stimulating agent comprises a CD27 agonist, such as an agonistic CD27 antibody. Suitable CD27 antibodies include, for example, varlilumab (CDX-1127).

In some embodiments, the at least one immune stimulating agent comprises MGA271, which targets B7H3 (WO11/109400).

In some embodiments, the at least one immune stimulating agent comprises a KIR antagonist, such as lirilumab.

In some embodiments, the at least one immune stimulating agent comprises an IDO antagonist. IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) or F001287.

In some embodiments, the at least one immune stimulating agent comprises a Toll-like receptor agonist, e.g., a TLR2/4 agonist (e.g., *Bacillus* Calmette-Guerin); a TLR7 agonist (e.g., Hiltonol or Imiquimod); a TLR7/8 agonist (e.g., Resiquimod); or a TLR9 agonist (e.g., CpG7909).

In some embodiments, the at least one immune stimulating agent comprises a TGF-β inhibitor, e.g., GC1008, LY2157299, TEW7197 or IMC-TR1.

In some embodiments, the CD80 ECD or CD80 ECD fusion molecule is administered to treat one of the above cancers in combination with an effective amount of a PD-1/PD-L1 inhibitor.

Exemplary PD-1/PD-L1 Inhibitors

PD-1/PD-L1 inhibitors include antibodies, fusion proteins, and peptides. A nonlimiting exemplary fusion protein that is a PD-1/PD-L1 inhibitor is AMP-224 (Amplimmune, GlaxoSmithKline). A nonlimiting exemplary peptide that is a PD-1/PD-L1 inhibitor is AUR-012. Other exemplary PD-1/PD-L1 inhibitors include antibodies that inhibit PD-1, such as anti-PD-1 antibodies and anti-PD-L1 antibodies. Such antibodies may be humanized antibodies, chimeric antibodies, mouse antibodies, and human antibodies.

In some embodiments, the combination results in an improved anti-tumor response in an animal cancer model, such as a xenograft model, compared to administration of either the CD80 ECD or CD80 ECD fusion molecule or PD-1/PD-L1 inhibitor alone. In some embodiments, the combination results in a synergistic response in an animal cancer model, such as a xenograft model, compared to administration of either the CD80 ECD or CD80 ECD fusion molecule or PD-1/PD-L1 inhibitor alone.

PD-1 is a key immune checkpoint receptor expressed by activated T and B cells and mediates immunosuppression. PD-1 is a member of the CD28 family of receptors, which includes CD28, CTLA4, ICOS, PD-1, and BTLA. Two cell surface glycoprotein ligands for PD-1 have been identified, Programmed Death Ligand-1 (PD-L1) and Programmed Death Ligand-2 (PD-L2). These ligands are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies (HuMAbs) that bind specifically to PD-1 with high affinity have been disclosed in U.S. Pat. No. 8,008,449. Other anti-PD-1 mAbs have been described in, for example, U.S. Pat. Nos. 6,808,710, 7,488, 802, 8,168,757 and 8,354,509, and PCT Publication No. WO 2012/145493. Each of the anti-PD-1 HuMAbs disclosed in U.S. Pat. No. 8,008,449: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and/or (j) inhibits tumor cell growth in vivo. Anti-PD-1 antibodies usable in the present invention include antibodies that bind specifically to human PD-1 and exhibit at least one, at least two, at least three, at least four or at least five of the preceding characteristics (a) through (j).

In one embodiment, the anti-PD-1 antibody is nivolumab. Nivolumab (also known as "Opdivo®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9): 846-56).

In another embodiment, the anti-PD-1 antibody is pembrolizumab. Pembrolizumab (also known as "Keytruda®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also the site with the address: "www" dot "cancer" dot "gov" slash "drugdictionary?cdrid=695789" (last accessed: Dec. 14, 2014). Pembrolizumab has been approved by the FDA for the treatment of relapsed or refractory melanoma.

In other embodiments, the anti-PD-1 antibody is MEDI0608 (formerly AMP-514), which is a monoclonal antibody against the PD-1 receptor. MEDI0608 is described, for example, in U.S. Pat. No. 8,609,089, B2 or at www "dot" cancer "dot" gov "slash" drugdictionary?cdrid=756047 (last accessed Dec. 14, 2014).

In some embodiments, the anti-PD-1 antibody is Pidilizumab (CT-011), which is a humanized monoclonal antibody. Pidilizumab is described in U.S. Pat. No. 8,686,119 B2 or WO 2013/014668 A1.

Anti-PD-1 antibodies usable in the disclosed methods also include isolated antibodies that bind specifically to human PD-1 and cross-compete for binding to human PD-1 with nivolumab (see, e.g., U.S. Pat. No. 8,008,449; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are monoclonal antibodies. For administration to human subjects, these cross-competing antibodies can be chimeric antibodies, or can be humanized or human antibodies.

Anti-PD-1 antibodies usable in the methods of the disclosed invention also include antigen-binding portions of the above antibodies. Examples include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Administration of CD80 ECDs or CD80 ECD Fusion Proteins in Combination with Immune Stimulating Agents or PD-1/PD-L1 Inhibitors In some embodiments, the CD80 ECD or CD80 ECD fusion molecule and the immune stimulating agent or PD-1/PD-L1 inhibitor are administered concurrently. In some embodiments, the CD80 ECD or CD80 ECD fusion molecule and the immune stimulating agent or PD-1/PD-L1 inhibitor are administered sequentially. In some embodiments, at least one, at least two, at least three doses, at least five doses, or at least ten doses of a CD80 ECD or CD80 fusion molecule is administered prior to administration of an immune stimulating agent or PD-1/PD-L1 inhibitor. In some embodiments, at least one, at least two, at least three doses, at least five doses, or at least ten doses of an immune stimulating agent or PD-1/PD-L1 inhibitor is administered prior to administration of a CD80 ECD or CD80 fusion molecule. In some embodiments, the last dose of immune stimulating agent or PD-1/PD-L1 inhibitor is administered at least one, two, three, five, days or ten, or one, two, three, five, twelve, or twenty four weeks prior to the first dose of CD80 ECD or CD80 fusion molecule. In some other embodiment, the last dose of CD80 ECD or CD80 fusion molecule is administered at least one, two, three, five, days or ten, or one, two, three, five, twelve, or twenty four weeks prior to the first dose of immune stimulating agent or PD-1/PD-L1 inhibitor. In some embodiments, a subject has received, or is receiving, immune stimulating agent or PD-1/PD-L1 inhibitor therapy, and a CD80 ECD or CD80 fusion molecule is added to the therapeutic regimen.

In some embodiments, the subject is an immune stimulating agent or PD-1/PD-L1 inhibitor inadequate responder (i.e. shows resistance to one or more immune stimulating agents or PD-1/PD-L1 inhibitors). A subject who is a PD-1/PD-L1 inhibitor inadequate responder, for example, may have previously responded to a PD-1/PD-L1 inhibitor, but may have become less responsive to the PD-1/PD-L1 inhibitor, or the subject may have never responded to the PD-1/PD-L1 inhibitor. Inadequate response to an immune stimulating agent or PD-1/PD-L1 inhibitor means that aspects of the condition that would be expected to improve following a standard dose of the PD-1/PD-L1 inhibitor do not improve, and/or improvement only occurs if greater than a standard dose is administered. In some embodiments, an immune stimulating agent or PD-1/PD-L1 inhibitor inadequate responder has experienced, or is experiencing, an inadequate response to the drug after receiving a standard dose for at least two weeks, at least three weeks, at least four weeks, at least six weeks, or at least twelve weeks. A "standard" dose of an immune stimulating agent or PD-1/PD-L1 inhibitor may be determined by a medical professional, and may depend on the subject's age, weight, healthy history, severity of disease, the frequency of dosing, etc. In some embodiments, an immune stimulating agent or PD-1/PD-L1 inhibitor inadequate responder has experienced, or is experiencing, an inadequate response to an anti-PD-1 antibody and/or an anti-PD-L1 antibody. In some embodiments, a PD-1/PD-L1 inhibitor inadequate responder has experienced, or is experiencing, an inadequate response to AMP-224. In some embodiments, a PD-1/PD-L1 inhibitor inadequate responder has experienced, or is experiencing, an inadequate response to a PD-1/PD-L1 inhibitor selected from nivolumab, pidilizumab, and pembrolizumab.

In any of the above embodiments, the combination of the CD80 ECD or CD80 ECD fusion molecule with the PD-1/PD-L1 inhibitor that is administered to the subject may inhibit tumor growth in a mouse syngeneic or xenograft cancer model over a period of 1 week, 10 days, or 2 weeks, for example, by at least 10%, at least 20%, at least 30%, at least 40%, at least 50%, at least 60%, at least 70%, at least 80%, at least 90%, at least 95%, or at least 98%. In any of the above combination therapy method embodiments, the combination of the CD80 ECD or CD80 ECD fusion molecule with the PD-1/PD-L1 inhibitor that is administered to the subject may reduce the volume of at least one tumor in the subject or in an animal model subject by at least 10%, at least 20%, at least 30%, at least 40%, at least 50%, at least 60%, at least 70%, at least 80%, at least 90%, at least 95%, or at least 98%, for example, over a period of one month, two months, three months, six months, or one year.

In any of these combination therapy methods, the CD80 ECD or CD80 ECD fusion molecule may be a CD80 ECD Fc comprising 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21.

Routes of Administration and Carriers

In various embodiments, polypeptides and fusion molecules may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding a polypeptide may be coated onto gold microparticles and delivered intradermally by a particle bombardment device, or "gene gun," as described in the literature (see, e.g., Tang et al., Nature 356:152-154 (1992)). The appropriate formulation and route of administration may be selected according to the intended application.

In various embodiments, polypeptide-comprising compositions are provided in formulations with a wide variety of pharmaceutically acceptable carriers (see, e.g., Gennaro, Remington: The Science and Practice of Pharmacy with Facts and Comparisons: Drugfacts Plus, $20^{th}$ ed. (2003); Ansel et al., Pharmaceutical Dosage Forms and Drug Delivery Systems, $7^{th}$ ed., Lippencott Williams and Wilkins (2004); Kibbe et al., Handbook of Pharmaceutical Excepients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising polypeptides and fusion molecules may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of a polypeptide or combination of polypeptides are also provided. In some embodiments, a unit dosage is provided wherein the unit dosage contains a predetermined amount of a composition comprising a polypeptide or combination of polypeptides, with or without one or more additional agents. In some embodiments, such a unit dosage is supplied in a single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, a PD-1/PD-L1 inhibitor, such as an antibody or fusion protein, is administered with the CD80 ECD or CD80 ECD fusion molecule at a dose of 1 to 4 mg/kg. In some embodiments, a PD-1/PD-L1 inhibitor is administered at a dose of 1, 2, 3, or 4 mg/kg.

Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of a CD80 ECD or CD80 ECD fusion molecule is administered to a subject one or more times. In various embodiments, an effective dose is administered to the subject once a month, less than once a month, such as, for example, every two months or every three months. In other embodiments, an effective dose is administered more than once a month, such as, for example, every three weeks, every two weeks or every week. In some embodiments, an effective dose is administered once per 1, 2, 3, 4, or 5 weeks. In some embodiments, an effective dose is administered twice or three times per week. An effective dose is administered to the subject at least once. In some embodiments, the effective dose may be administered multiple times, including for periods of at least a month, at least six months, or at least a year.

Additional Combination Therapies

CD80 ECDs or CD80 ECD fusion molecules may be administered alone, with PD-1/PD-L1 inhibitors, and/or with other modes of treatment. CD80 ECDs or CD80 ECD fusion molecules may be provided before, substantially contemporaneous with, or after other modes of treatment, for example, surgery, chemotherapy, radiation therapy, or the administration of another biologic. In some embodiments, the cancer has recurred or progressed following a therapy selected from surgery, chemotherapy, and radiation therapy, or a combination thereof.

For treatment of cancer, CD80 ECDs or CD80 ECD fusion molecules may be administered in conjunction with one or more additional anti-cancer agents, such as the chemotherapeutic agent, growth inhibitory agent, anti-angiogenesis agent and/or anti-neoplastic composition. Non-limiting examples of chemotherapeutic agent, growth inhibitory agent, anti-angiogenesis agent, anti-cancer agent and anti-neoplastic composition that can be used in combination with the antibodies of the present invention are provided in the following definitions.

In any of the above combination therapy method embodiments, the therapy administered to the subject may inhibit tumor growth in a mouse syngeneic or xenograft cancer model over a period of 1 week, 10 days, or 2 weeks, for example, by at least 10%, at least 20%, at least 30%, at least 40%, at least 50%, at least 60%, at least 70%, at least 80%, at least 90%, or at least 95%. In any of the above combination therapy method embodiments, the therapy administered to the subject may reduce the volume of at least one tumor in the subject or in an animal model subject by at least 10%, at least 20%, at least 30%, at least 40%, at least 50%, at least 60%, at least 70%, at least 80%, at least 90%, at least 95%, or at least 98%, for example, over a period of one month, two months, three months, six months, or one year.

In any of these further combination therapy methods, the CD80 ECD or CD80 ECD fusion molecule may be a CD80 ECD Fc comprising 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments the Fc domain comprises the amino acid sequence of SEQ ID NO:14. In some embodiments, the fusion molecule comprises the amino acid sequence of SEQ ID NO:20 or 21.

A "chemotherapeutic agent" is a chemical compound useful in the treatment of cancer. Examples of chemotherapeutic agents include, but are not limited to, alkylating agents such as thiotepa and Cytoxan® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Ill.), and Taxotere® doxetaxel (Rh6ne-Poulenc Rorer, Antony, France); chlorambucil; Gemzar® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and Fareston® toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (Avastin®)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (Taxotere®, Rhone-Poulenc Rorer), derived from the European yew, is a semisynthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, other cancer immunotherapeutic agents aside from PD-1/PD-L1 inhibitors, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, CTLA-4 inhibitors (e.g., anti-CTLA antibody ipilimumab (YERVOY®)), PD-L2 inhibitors (e.g., anti-PD-L2 antibodies), TIM3 inhibitors (e.g., anti-TIM3 antibodies), cytokines, antagonists (e.g., neutralizing antibodies) that bind to one or more of the following targets ErbB2, ErbB3, ErbB4, PDGFR-beta, BlyS, APRIL, BCMA, PD-L2, CTLA-4, TIM3, or VEGF receptor(s), TRAIL/Apo2, and other bioactive and organic chemical agents, etc. Combinations thereof are also included in the invention.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: A CD80 ECD Fc Fusion Molecule Reduces Tumor Growth in Mice Implanted with Murine Colorectal Carcinoma Cell Line CT26

Seven-week old female BALB/c mice were purchased from Charles River Laboratories (Hollister, Calif.) and were acclimated for two weeks before the start of the study. The murine colorectal carcinoma cell line CT26 was implanted subcutaneously over the right flank of the mice at $1.0 \times 10^6$ cells/200 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and Matrigel® at $5 \times 10^6$ cells per milliliter.

Mice were monitored twice-weekly following cell implantation for tumor growth. For tumor measurements, the length and width of each tumor was measured using calipers and volume was calculated according to the formula: Tumor volume $(mm^3)$=(width $(mm)\times$length $(mm))^2/2$. On Day 7, all tumors were measured, and mice were randomly assigned to treatment groups. The mean tumor volume for all animals enrolled into treatment groups was 175 $mm^3$. Mice were administered Saline or plasmid DNA via RIPPS$^{SM}$. Plasmid DNA that was administered via RIPPS$^{SM}$ contained the sequence for the extracellular domain (ECD) of murine CD80 or CTLA4 as well as the Fc domain of human IgG2a. Tumors continued to be measured at least twice per week until tumor volume exceeded 10% of animal weight, or approximately 2000 $mm^3$.

Figure 1A:
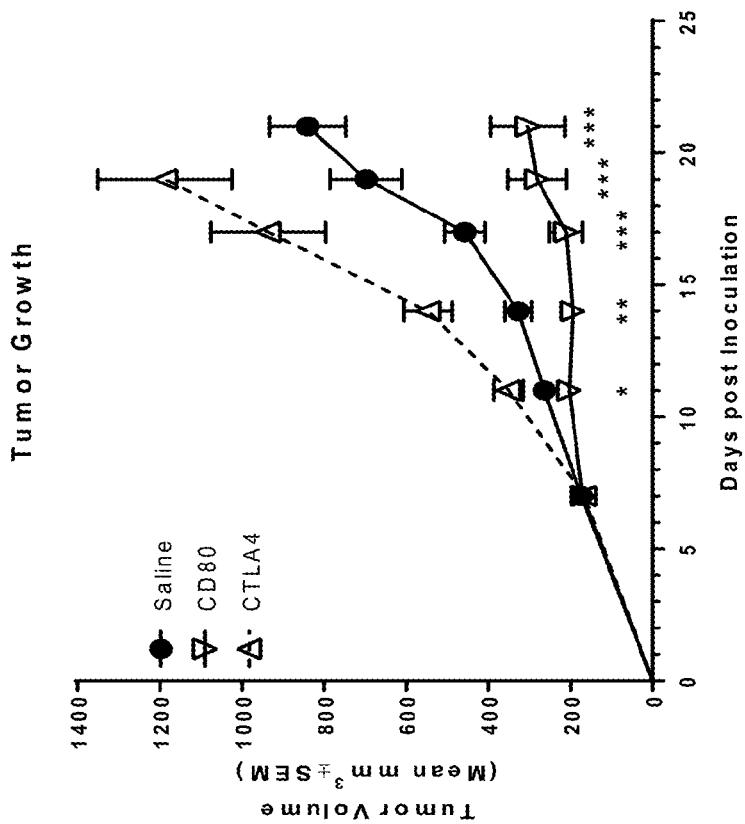

The change in tumor size is shown by graphing mean tumor volume relative to the day upon which animals were inoculated with CT26 cells. (FIG. 1a.) RIPPS with mouse CD80 ECD significantly reduced tumor growth compared to Saline control (p<0.05) beginning on Day 11. (FIG. 1a-b.) P-values were calculated using unpaired, two-tailed t-test analyses of the calculated tumor volumes on each day of the study (*p<0.05, p<0.01, *p<0.001). Tumor growth inhibition by CD80 ECD was determined to be 78.8% compared to saline control, which was calculated as 100× (1–(mean change in tumor volume for CD80/mean change in tumor volume for saline)). As also shown in FIG. 1a, RIPPS with mouse CTLA4-ECD Fc actually enhanced tumor growth compared to the saline control. One explanation for this result is that the CTLA4-ECD Fc construct might have acted as a ligand trap for CD80, preventing CD80 from binding to CD28 and stimulating T cell activity against tumor cells.

Example 2: A CD80 ECD Fc Fusion Molecule in Combination with an Anti-PD-1 Antibody Reduces Tumor Growth in Mice Implanted with Murine Colorectal Carcinoma Cell Line CT26

Seven-week old female BALB/c mice were purchased from Charles River Laboratories (Hollister, Calif.) and were acclimated for 12 days before the start of the study. The murine colorectal carcinoma cell line CT26 was implanted subcutaneously over the right flank of the mice at $1.0 \times 10^6$ cells/200 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and Matrigel® at $5 \times 10^6$ cells per milliliter.

Mice were monitored twice-weekly following cell implantation for tumor growth. For tumor measurements, the length and width of each tumor was measured using calipers and volume was calculated according to the formula: Tumor volume $(mm^3)$=(width $(mm)\times$length $(mm))^2/2$. On Day 7, all tumors were measured, and mice were randomly assigned to treatment groups. The mean tumor volume for all animals enrolled into treatment groups was approximately 150 $mm^3$. Mice were administered plasmid DNA coding for mouse CD80 ECD plus Fc from human IgG2a or Fc alone (negative control) via RIPPS$^{SM}$. Protein was administered for anti-PD1 (Clone RMP1-14) or Rat IgG2a (Clone 2A3, negative control). Dosing groups were as follows: 1) Fc RIPPS$^{SM}$ plus Rat IgG2a, 2) CD80 RIPPS$^{SM}$ plus Rat IgG2a, 3) Fc RIPPS$^{SM}$ plus anti-PD1, or 4) CD80 RIPPS$^{SM}$ plus anti-PD1. Tumors continued to be measured at least twice per week until tumor volume exceeded 10% of animal weight, or approximately 2000 $mm^3$.

Figure 2B:
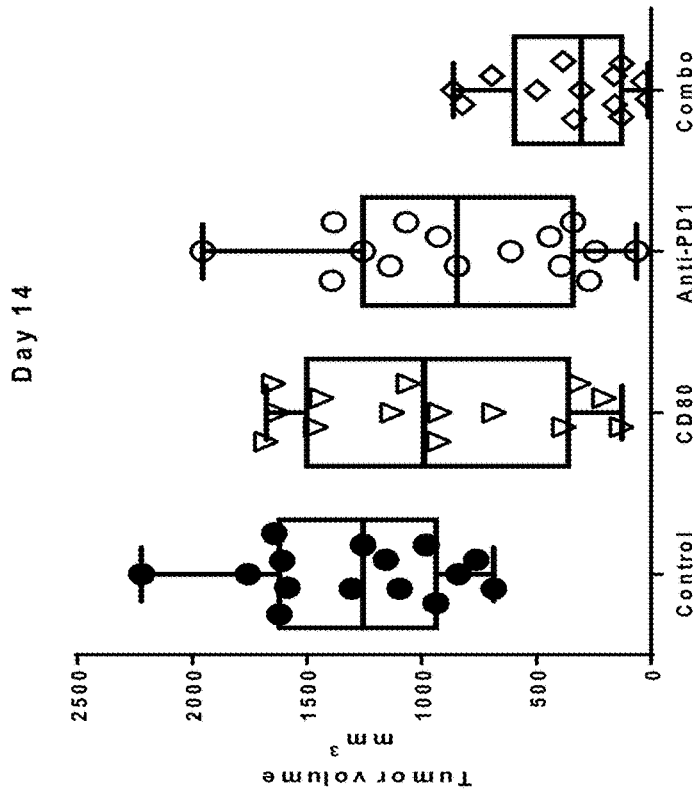
FIGS. 2a-2b show effects of administering a CD80 ECD Fc fusion molecule or an anti-PD-1 antibody or a combination of the two compared to a saline control to mice implanted with murine colorectal carcinoma cell line CT26 cells.
Figure 2A:
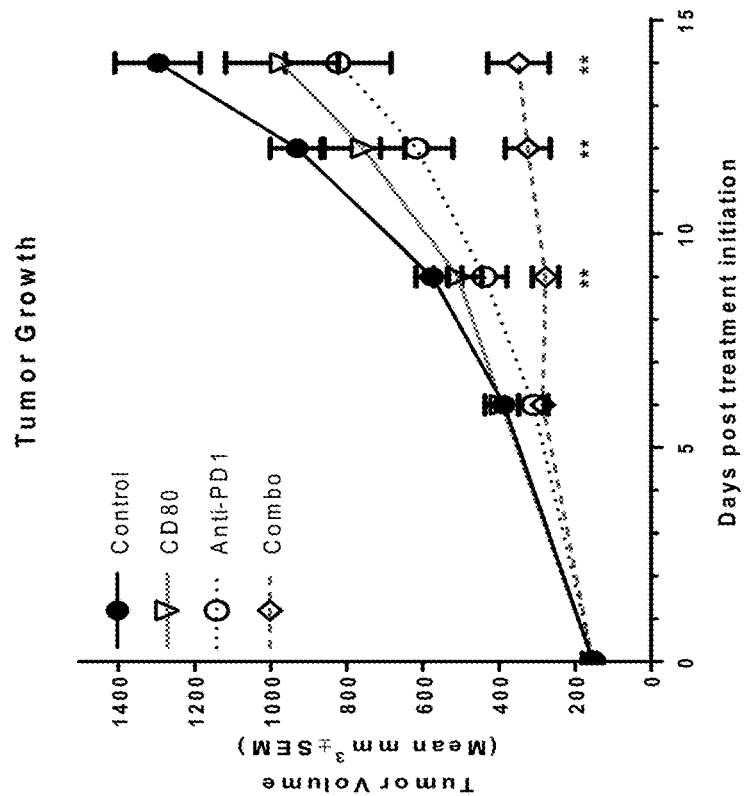

The change in tumor size is shown by graphing mean tumor weight for all groups at the end of the study. (FIG. 2a.) RIPPS$^{SM}$ with mouse CD80 ECD or administration of anti-PD1 reduced tumor growth compared to control. (FIG. 2a-b.) The combination of CD80 RIPPS$^{SM}$ and anti-PD1 resulted in significantly reduced tumor growth compared to either CD80 (p<0.01 beginning after Day 9) or anti-PD-1 (p<0.01 on Day 14) alone (p<0.05) beginning nine days after treatment initiation. P-values were calculated using unpaired, two-tailed t-test analyses of the calculated tumor volumes on each day of measurement.

Tumor growth inhibition (TGI) by CD80 ECD and anti-PD1 were determined to be 28.7% and 41.5%, respectively, compared to control. TGI by the combination of CD80 ECD and anti-PD1 combination was determined to be 83%. (See FIG. 2b.) TGI was calculated using the formula 100×(1– (Mean Δvolume Treatment group/Mean Δvolume Saline).

Example 3: Comparison of Activity of CD80 ECD Fc Fusion Molecules with Wild-Type and Mutant Human IgG1 Fc Fusion Polypeptide Sequences Seven-week old female BALB/c mice were purchased from Charles River Laboratories (Hollister, Calif.) and were acclimated for two weeks before the start of the study. The murine colorectal carcinoma cell line CT26 was implanted subcutaneously over the right flank of the mice at $1.0 \times 10^6$ cells/200 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and Matrigel® at 5×10⁶ cells per milliliter.

Mice were monitored twice-weekly following cell implantation for tumor growth. For tumor measurements, the length and width of each tumor was measured using calipers and volume was calculated according to the formula: Tumor volume $(mm^3)$=(width (mm)×length $(mm))^2/2$. On Day 5, all tumors were measured, and mice were randomly assigned to treatment groups. The mean tumor volume for all animals enrolled into treatment groups was 175 $mm^3$. Mice were administered Saline or plasmid DNA via RIPPS$^{SM}$. Plasmid DNA that was administered via RIPPS$^{SM}$ contained the sequence for the extracellular domain (ECD) of murine CD80 with the Fc domain of human IgG1. Two clones were administered via RIPPS$^{SM}$, one with the wild type human IgG1 Fc (CD80-IgG1 WT) and the other with this Fc bearing three mutated amino acids (L234F/L235E/P331S) in order to alter the interaction of Fc with Fc gamma receptors (CD80-IgG1 MT). Tumors continued to be measured at least twice per week until tumor volume exceeded 10% of animal weight, or approximately 2000 $mm^3$.

Figures 3A, 3B:
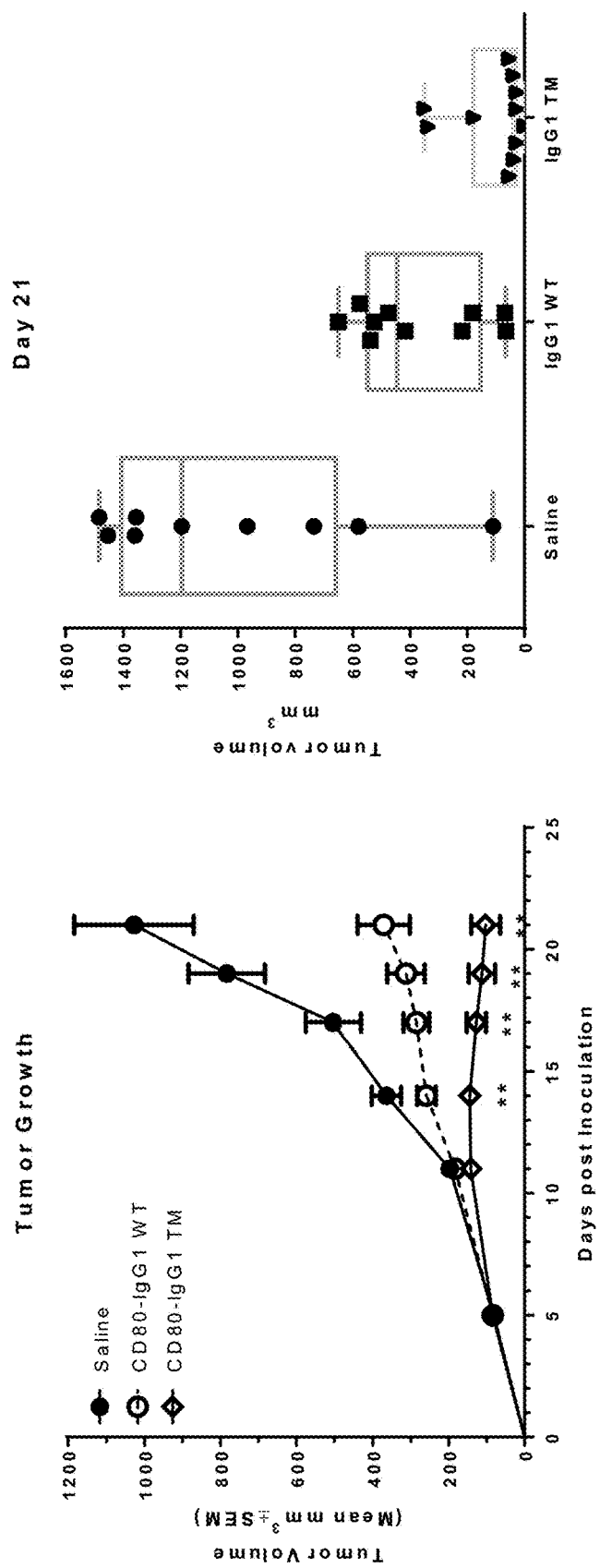
FIGS. 3a-b show the effect of the Fc fusion polypeptide sequence on effects of a CD80 ECD Fc fusion molecule on tumor growth of the CT26 tumors in mice. Specifically, mice were administered saline control, or a CD80 ECD Fc with a human IgG1 wild-type Fc domain fusion partner (CD80-IgG1 WT), or with a CD80 ECD Fc with a mutant (L234F/L235E/P331S) human IgG1 Fc domain fusion partner (CD80-IgG1 MT).

The change in tumor size is shown by graphing mean tumor volume relative to the day upon which animals were inoculated with CT26 cells. (FIG. 3a-b.) RIPPS$^{SM}$ with CD80-IgG1 WT significantly reduced tumor growth compared to Saline control ($p<0.05$) beginning on Day 14. CD80-IgG MT significantly reduced tumor growth compared to CD80-IgG1 WT ($p<0.01$) beginning on Day 14. P-values were calculated using unpaired, two-tailed t-test analyses of the calculated tumor volumes on each day of the study (* $p<0.05$, ** $p<0.01$). Tumor growth inhibition (TGI) by CD80-IgG1 WT was determined to be 69.4% compared to Saline control, compared to TGI for CD80-IgG MT, which was calculated as 98%. (See FIG. 3b.) TGI was determined using the formula 100×(1−(Mean Δvolume Treatment group/Mean Δvolume Saline).

Example 4: Effects of CD80 ECD Fc Fusion Molecules with Wild-Type and Mutant Human IgG1 Fc Fusion Polypeptide Sequences on Infiltrating T Cells in CT26 Tumors A separate in vivo study was conducted to analyze the effects of the CD80-IgG1 WT and CD80-IgG1 MT on infiltrating T cells in CT26 tumors at an early stage of the treatment.

Seven-week old female BALB/c mice were purchased from Charles River Laboratories (Hollister, Calif.) and were acclimated for two weeks before the start of the study. The murine colorectal carcinoma cell line CT26 was implanted subcutaneously over the right flank of the mice at 1.0×10⁶ cells/200 μl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and Matrigel® at 5×10⁶ cells/mL.

Mice were monitored twice-weekly following cell implantation for tumor growth. For tumor measurements, the length and width of each tumor was measured using calipers and volume was calculated according to the formula: Tumor volume $(mm^3)$=(width (mm)×length $(mm))^2/2$. On Day 5, all tumors were measured, and mice were randomly assigned to treatment groups (n=5 mice per group). The mean tumor volume for all animals enrolled into treatment groups was 72 $mm^3$. Mice were administered saline, a murine extracellular domain (ECD) of CD80 with a wild type human IgG1 Fc (CD80-IgG1 WT), or a murine ECD of CD80 with a mutated human IgG1 Fc (CD80-IgG1 MT, mutated L234F/L235E/P331S) in order to alter the interaction with Fc gamma receptors. Tumors were measured on Days 5 and 11.

On Day 12, mice were euthanized with $CO_2$ and perfused with phosphate-buffered saline (PBS), pH 7.4. Briefly, the mouse chest was opened rapidly, and a syringe with 20-gauge needle was used to infuse 40 mL of PBS into the aorta via an incision in the left ventricle. Blood and PBS exited through an opening in the right atrium. The tumors were removed and immersed in 10% neutral buffered formalin at 4° C. After 2 hours the tissues were rinsed 3 times in PBS and then transferred in 30% sucrose in PBS overnight. The next day the tumors were frozen in OCT compound and stored at −80 C.

Cryostat sections were cut at 20-μm in thickness. Sections were dried on Superfrost® Plus slides for 1 to 2 hours. Specimens were permeabilized with PBS containing 0.3% Triton® X-100 and incubated in 5% goat normal serum in PBS 0.3% Triton® X-100 (blocking solution) for 1 hour at room temperature to block nonspecific antibodies binding. To detect T-cells, sections were incubated with rat-anti-CD4 (GK1.5/eBiosciences) and rabbit anti-CD3 antibody (SP7/Thermo Scientific) both diluted 1:500 in blocking solution overnight. Control specimens were incubated in 5% normal serum instead of primary antibody for the same period. After rinsing with PBS containing 0.3% Triton® X-100, specimens were incubated for 4 hours at room temperature with Alexa® 594-labeled goat anti-rat and Alexa® 488-labeled goat anti-rabbit secondary antibodies diluted 1:400 in PBS (Jackson ImmunoResearch). Specimens were rinsed with PBS containing 0.3% Triton® X-100, fixed in 1% paraformaldehyde (PFA), rinsed again with PBS, and mounted in Vectashield antifade mounting medium with DAPI (Vector laboratories).

Specimens were examined with a Zeiss Axiophot® 2 plus fluorescence microscope equipped with AxioCam® HRc camera. Representative images for each experimental group showing the amount and distribution of the $CD3^+$ and $CD4^+$ cells within the tumor were collected and are shown in FIGS. 4a and 4b.

Figure 4A:
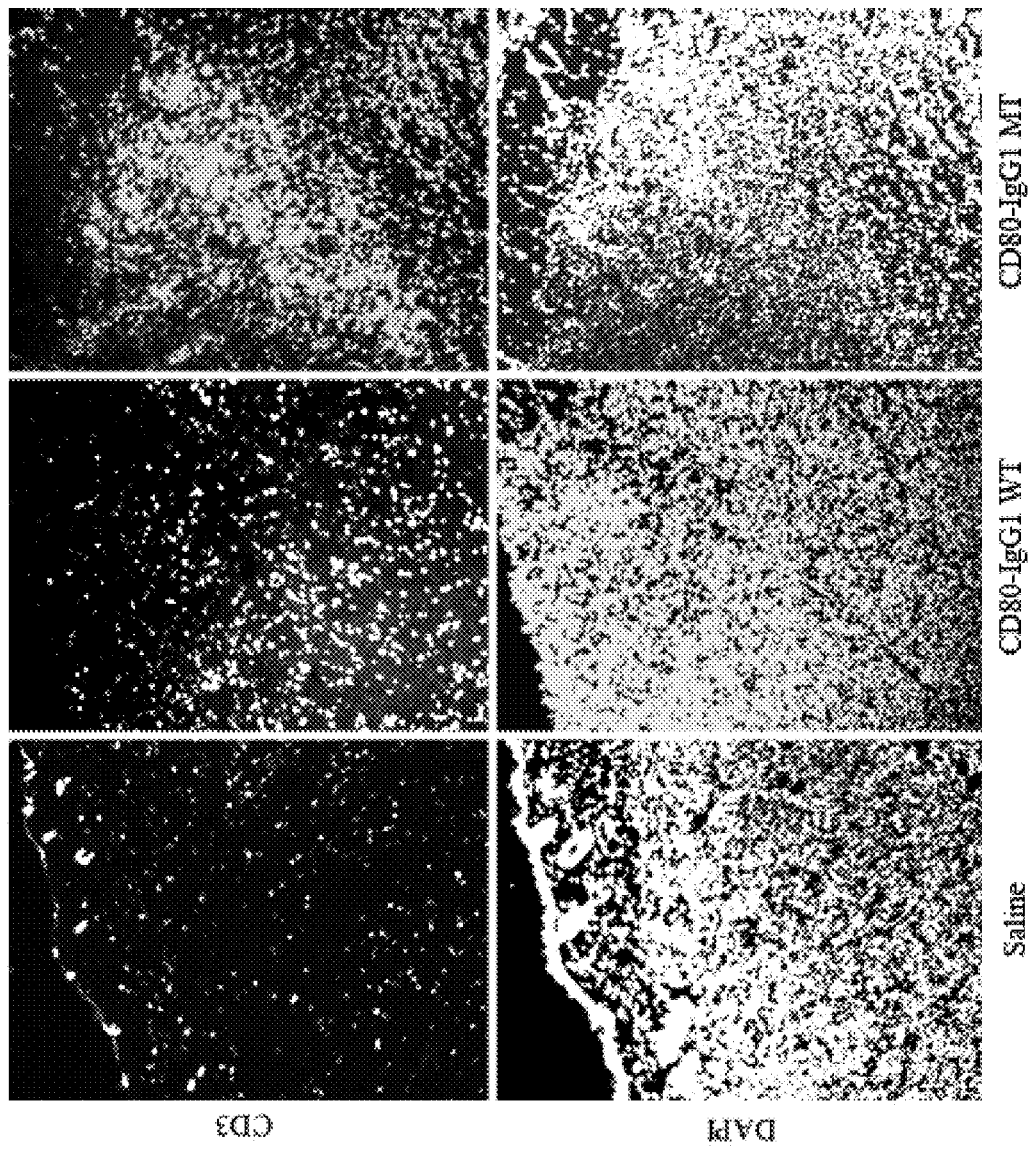
FIGS. 4a-b show staining of murine tumor cells for presence of CD3+ and CD4+ T cells after exposure to saline control or to CD80 ECD Fc fusion molecules with either wild-type and mutant Fc fusion partners.
Figure 4B:
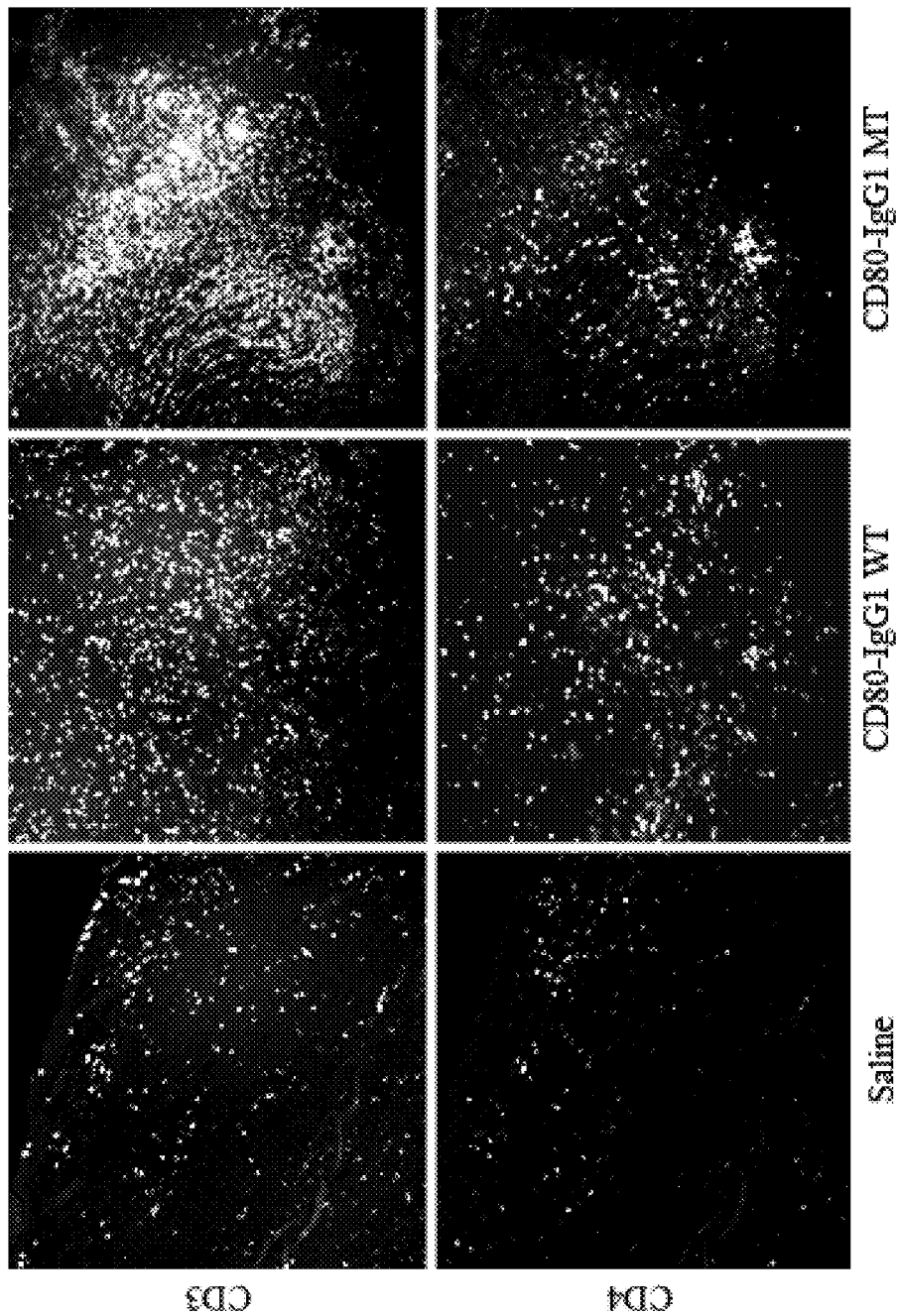

Treatment with CD80-IgG1 WT or CD80-IgG1 MT increased the number of intratumoral $CD3^+$ and CD4+ cells compared to saline (FIGS. 4a and 4b). While the amount of CD4+ cells was similar between the CD80-IgG1 WT or CD80-IgG1 MT treated tumors, treatment with CD80-IgG1 MT led to a greater increase of tumor infiltrating $CD3^+$ T cells compared to CD80-IgG1 WT (FIG. 4b). The ratio of CD3+ to CD4+ cells was increased with the CD80-IgG1 MT compared to the CD80-IgG1 WT.

Example 5: Cytokine Release Effects of a CD80 ECD Fc Fusion Molecule

Methods
Protein Treatments

A human CD80 ECD IgG1 Fc fusion molecule (CD80-Fc) was bound to magnetic protein-A beads (Life Technologies) in T-cell proliferation media containing RPMI 1640, 100 IU Penicilin/100 ug/ml Streptomycin, 2 mM L-Glutamine, 100 nM non-essential amino acids, 55 uM 2-mercaptoethanol and 10% ultra low-IgG fetal bovine serum. Binding reactions were carried out in 96 well flat-bottom tissue culture plates at a volume of 100 ul per well with a bead concentration of 3 million beads per ml. CD80-Fc was bound to the beads across a series of concentrations: 10, 1, 0.1 ug/ml. An additional set of binding reactions was also performed with the addition of 3 ng/ml OKT3-scFv. Proteins were allowed to bind for 1 hour at room temperature on a rocking platform, following which 100 ul of 20 ug/ml (final concentration 10 ug/ml) IgG1 Free-Fc (FPT) was added to each well and allowed to bind for an additional hour in order to block any unoccupied Protein-A binding sites on the beads. The fully loaded and blocked beads were then washed 3 times with PBS using a magnetic 96-well plate stand in order to remove unbound proteins. 100 ul of Human Pan T-cells at a concentration of $1 \times 10^6$ cells/ml was then added to each well of dry, washed beads. Each condition was tested in triplicate.

Cells

Human PBMCs were isolated from apheresis-enriched blood (buffy coats) collected from healthy donors ~18 hrs prior to isolation using Ficoll® (Biochrom) gradient density centrifugation. Pan T-cells were then isolated from PBMCs using a Human Pan T-cell isolation kit (Miltenyi). T-cells were seeded at a density of 1 million cells/ml in T225 tissue culture flasks in proliferation media (above) supplemented with 8 ng/ml IL-2 and Human T-cell Activator Dynabeads® (Life Tech) 1 bead/cell. Following seeding, cells were fed with fresh IL-2 and continually kept at a concentration of 0.3 million cells/ml by the addition of fresh proliferation media every 2 days. Cells were kept in a 37° C. water-jacketed incubator maintained at 5% $CO_2$. After 6 days of expansion, the activator-beads were removed using a magnetic tube stand and the cells were resuspended at a concentration of 1 million cells/ml in fresh proliferation media without IL-2. 24 hours later the cells were put into assay with Protein-A bead immobilized proteins.

Cytokine Measurements

Soluble Interferon Gamma (IFN-γ) and Tumor Necrosis Factor Alpha (TNF-α) levels were measured in the supernatants using HTRF-ELISA kits (Cisbio) 24 hours after the cells had been treated with the Protein-A bead immobilized proteins according to the manufacturer's instructions.

Results

Figures 5A, 5B:
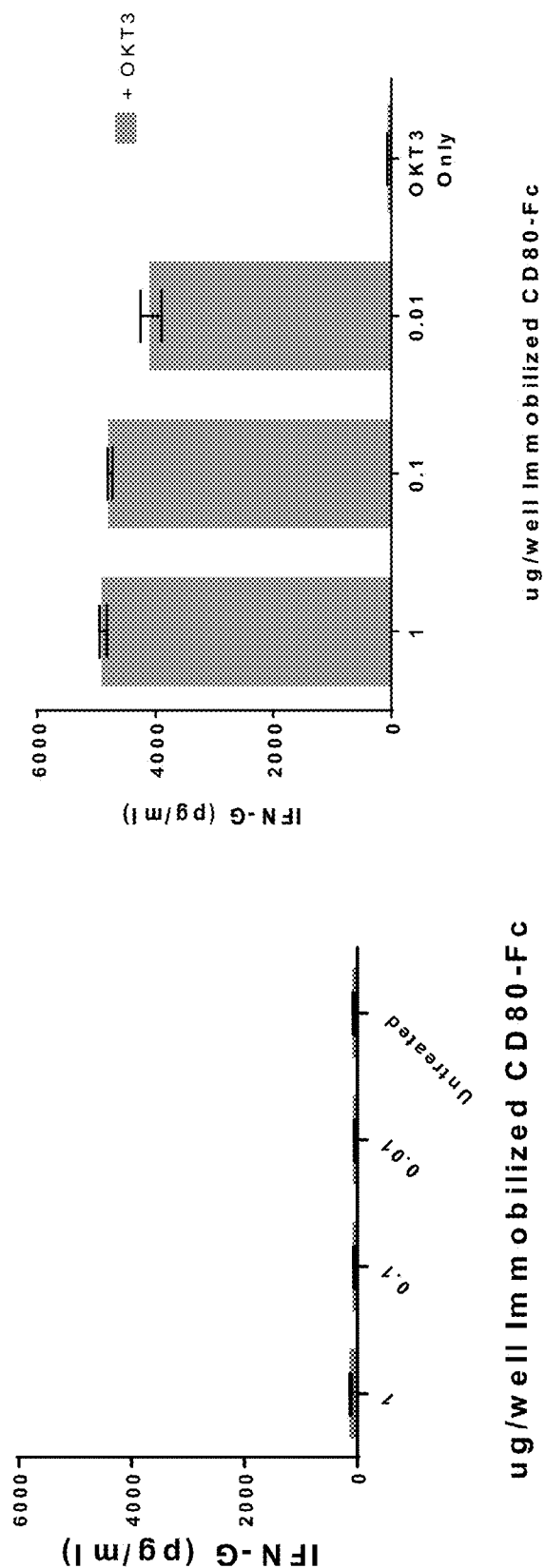
FIGS. 5a-d show release of cytokines IFN-γ and TNF-α from T-cells on 96 well tissue culture plates exposed to protein A beads coated with 0.01, 0.1, or 1 μg/well of a CD80 ECD IgG1 Fc domain fusion molecule (CD80-Fc).
Figures 5C, 5D:
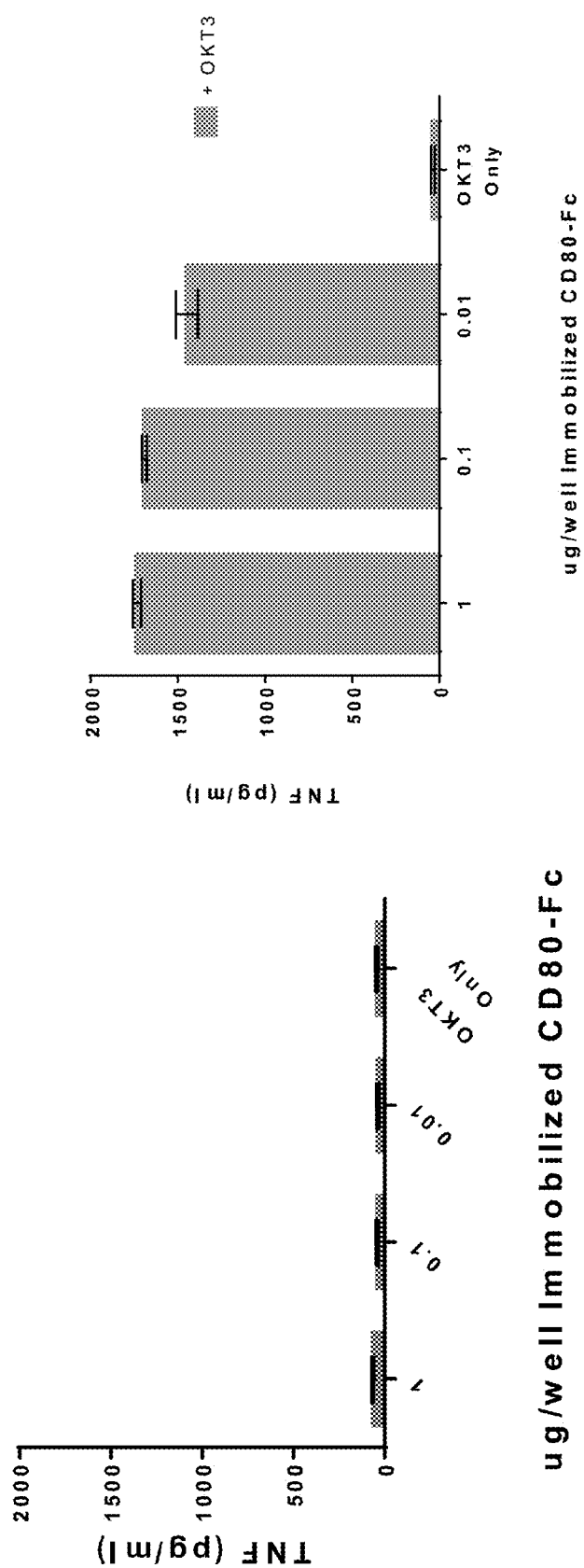

Bead-immobilized CD80-Fc alone did not cause significant human T-cell activation, as measured by soluble cytokine production (FIGS. 5a & c). However, when a small amount of OKT3-scFv was immobilized along with CD80-Fc, robust CD80-dependent IFN-γ and TNF-α release was observed (FIGS. 5b & d). The amount of OKT3-scFv used here was too low to cause T-cell stimulation on its own and therefore required the presence of CD80 as a co-stimulatory protein. These results therefor confirm the CD80-Fc used in this assay was indeed biologically active.

While release of IFN-γ and TNF-α in this assay showed that the CD80-Fc was biologically active, an excessive release of cytokines such as IFN-γ and TNF-α can be harmful. Thus, to address the potential safety of CD80 ECD Fc treatment, these results were compared to earlier published results with TGN1412, a monoclonal anti-CD28 antibody that was shown to be a T-cell "superagonist" and to release excessive and harmful levels of cytokines such as IFN-γ and TNF-α in human subjects.

Immobilized TGN1412 alone appears to be significantly more potent at inducing cytokine release from human T-cells than human CD80 alone. Findlay et al., *J. Immunological Methods* 352: 1-12 (2010), reported that 1 ug/well of TGN1412 caused robust TNFα release, ~2000 pg/ml, and Vessillier et al., *J. Immunological Methods* 424: 43-52 (2015), reported the same amount of TGN1412 caused robust IFN-γ, ~10000 pg/ml. In our assay, the same amount of immobilized CD80-Fc did not cause significant release of either cytokine. These results suggest that CD80-Fc is at least 1000-fold less potent at inducing cytokine release compared to TGN1412 and therefore poses a significantly lower risk of inducing cytokine storm in humans than TGN1412.

Example 6: Effects of a CD80 ECD Fc Fusion Molecule on CT26 Tumors In Vivo with Fc Domains with Different Sialic Acid (SA) Content An in vivo study was conducted in CT26 tumors to analyze the effects of three different lots of CD80 ECD fused to wild-type human IgG1 Fc having different sialic acid (SA) contents. Specifically, lot E of the CD80 ECD Fc contains 20 mol SA/mol protein, lot D contains 15 mol SA/mol protein, and lot A contains 5 mol SA/mol protein.

Seven week old female BALB/c mice were purchased from Charles River Laboratories (Hollister, Calif.) and were acclimated for one week before the study was initiated. The murine colorectal carcinoma cell line CT26 was implanted subcutaneously over the right flank of the mice at $1.0 \times 10^6$ cells/200 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and Matrigel® at $5 \times 10^6$ cells per milliliter.

Mice were monitored for tumor growth twice weekly following cell implantation. For tumor measurements, the length and width of each tumor was measured using calipers and volume was calculated according to the formula: tumor volume $(mm^3)=(width\ (mm) \times length\ (mm))^2/2$. On Day 7, all tumors were measured, and mice were randomly assigned to seven treatment groups (n=10 mice per experimental group). The mean tumor volume for all animals enrolled was 94 $mm^3$. The first group was injected with 200 µl of PBS (control) intravenously (i.v.) into the tail vein. The second group was injected with CD80 ECD Fc at 20 mol SA/mol protein (lot E) i.v. dosed at 0.3 mg/kg. The third group was injected with CD80 ECD Fc at 20 mol SA/mol protein (lot E) i.v. dosed at 0.6 mg/kg. The fourth group was injected with CD80 ECD Fc at 15 mol SA/mol protein (lot D) i.v. dosed at 0.3 mg/kg. The fifth group was injected with CD80 ECD Fc at 15 mol SA/mol protein (lot D) i.v. dosed at 0.6 mg/kg. The sixth group was injected with CD80 ECD Fc at 5 mol SA/mol protein (lot A) i.v. dosed at 0.3 mg/kg. The seventh group was injected with CD80 ECD Fc at 5 mol SA/mol protein (lot A) i.v. dosed at 0.6 mg/kg. Tumors were measured on day 10, 14, 16, 18, 22, 24.

Figure 6:
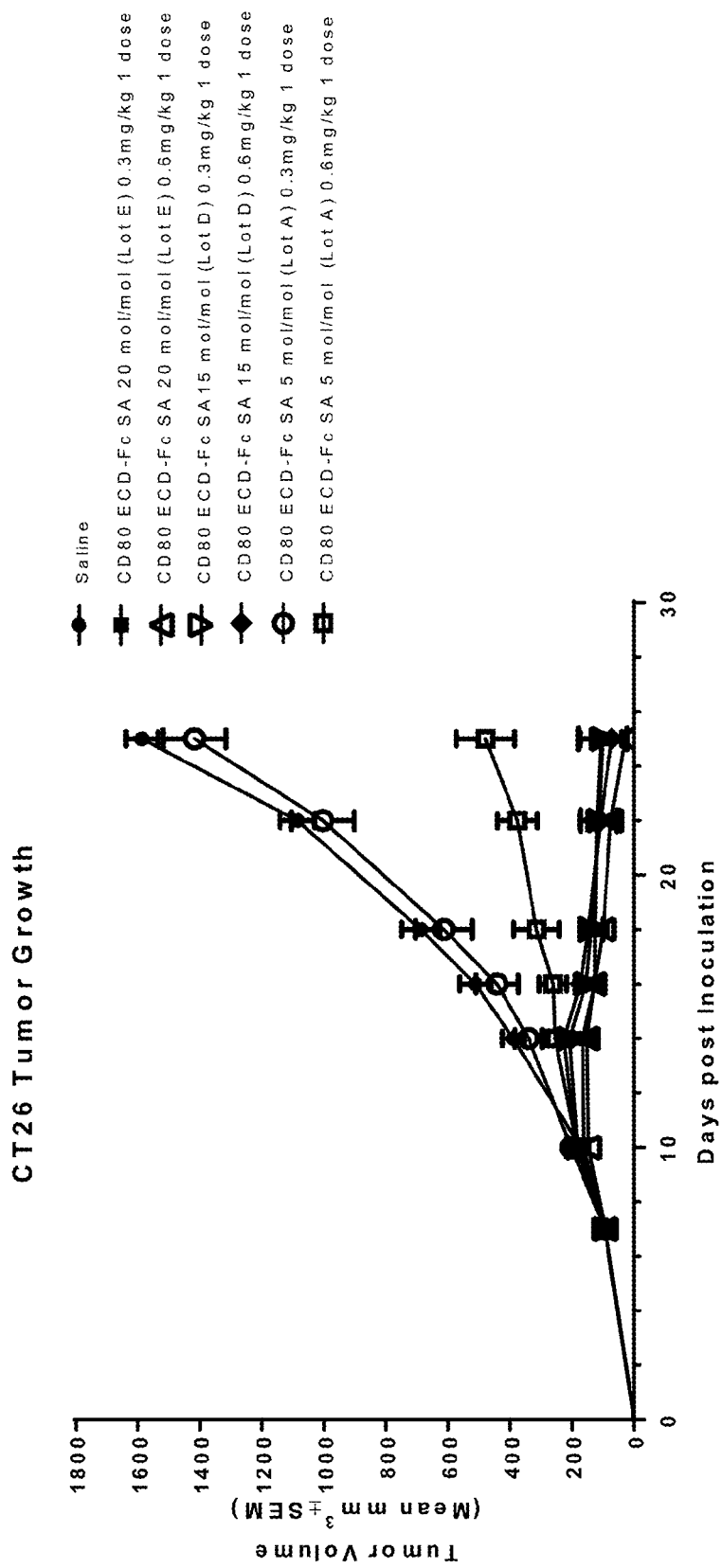
FIG. 6 shows tumor growth of murine CT26 tumors following treatment with a saline control or either 0.3 or 0.6 mg/kg doses of three different lots of a CD80 ECD Fc fusion molecule having three different sialic acid (SA) contents. Lot A has 5 mol SA/mol protein, lot D has 15 mol SA/mol protein and lot E has 20 mol SA/mol protein. Treatment with CD80 ECD Fc lot E dosed at 0.3 or 0.6 mg/kg resulted in a 93% and 98% inhibition of tumor growth compared to the control (P<0.001). Treatment with CD80 ECD Fc lot D dosed at 0.3 or 0.6 mg/kg resulted in a 93% and 95% inhibition of tumor growth compared to the control (P<0.001). By comparison, treatment with CD80 ECD Fc lot A at 0.3 mg/kg did not inhibit tumor growth compared to the control and when dosed at 0.6 mg/kg it only induced 70% inhibition (P<0.001) of tumor growth.

Treatment with CD80 ECD Fc at 20 mol SA/mol protein (lot E) dosed at 0.3 or 0.6 mg/kg resulted in a 93% and 98% inhibition of tumor growth compared to the control (P<0.001). Treatment with CD80 ECD Fc at 15 mol SA/mol protein (lot D) dosed at 0.3 or 0.6 mg/kg resulted in a 93% and 95% inhibition of tumor growth compared to the control (P<0.001). By comparison, treatment with CD80 ECD Fc lot A at 0.3 mg/kg (with 5 mol SA/mol protein) did not inhibit tumor growth compared to the control and when dosed at 0.6 mg/kg it only induced 70% inhibition (P<0.001) (FIG. 6).

The incidence of tumor-free mice was analyzed at day 37. Treatment with CD80 ECD-Fc at 20 mol/mol SA (lot E) dosed at 0.3 or 0.6 mg/kg led to complete tumor regression in 8/10 (80%) or 10/10 (100%) of the mice. Treatment with CD80 ECD-Fc at 15 mol/mol SA (lot D) dosed at 0.3 or 0.6 mg/kg led to complete tumor regression in 9/10 (90%) of the mice. By comparison, treatment with CD80 ECD-Fc lot A dosed at 0.6 mg/kg induced tumor regression only in 1/10 (10%) of the mice, as shown in the table below.

| Treatment group | Tumor free mice at day 37 |
| --- | --- |
| Saline | 0% (0/10 mice) |
| CD80 ECD-Fc SA 20 mol/mol (lot E) at 0.3 mg/kg 1 dose | 80% (8/10 mice) |
| CD80 ECD-Fc SA 20 mol/mol (lot E) at 0.6 mg/kg 1 dose | 100% (10/10 mice) |
| CD80 ECD-Fc SA 15 mol/mol (lot D) at 0.3 mg/kg 1 dose | 90% (9/10 mice) |
| CD80 ECD-Fc SA 15 mol/mol (lot D) at 0.6 mg/kg 1 dose | 90% (9/10 mice) |
| CD80 ECD-Fc SA 5 mol/mol (lot A) at 0.3 mg/kg 1 dose | 0% (0/10 mice) |
| CD80 ECD-Fc SA 5 mol/mol (lot A) at 0.6 mg/kg 1 dose | 10% (1/10 mice) |

Example 7: Effects of a Murine CD80 ECD—Murine Fc Fusion Molecule on Tumor Growth in Three Different Syngeneic Tumor Models In vivo studies were conducted using a mouse surrogate comprising the extracellular domain (ECD) of murine CD80 linked to the Fc domain of mouse IgG2a wild type (murine CD80 ECD-Fc). The effects of murine CD80 ECD-Fc were compared with those of the anti-CTLA4 antibody clone 9D9 (IgG2b) in three different syngeneic tumor models: the CT26 colon carcinoma, the MC38 colon carcinoma and the B16 melanoma models.

CT26 Tumor Model

Seven week old female BALB/c mice were purchased from Charles River Laboratories (Hollister, Calif.) and were acclimated for one week before the study was initiated. The murine colorectal carcinoma cell line CT26 was implanted subcutaneously over the right flank of the mice at $1.0\times10^6$ cells/200 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and matrigel.

Mice were monitored twice weekly following cell implantation for tumor growth. For tumor measurements, the length and width of each tumor was measured using calipers and volume was calculated according to the formula: tumor volume $(mm^3)=(width\ (mm)\times length\ (mm))^2/2$. On Day 7, all tumors were measured, and mice were randomly assigned to seven treatment groups (n=15 mice per experimental group). The mean tumor volume for all animals enrolled was 96 $mm^3$. Mice were dosed 3 times, on day 4, 7 and 11. The first group was injected with mouse IgG2b (mIgG2b) i.p. dosed at 10 mg/kg (control). The second group was injected with murine CD80 ECD-Fc 20 mol/mol SA i.v. dosed at 0.3 mg/kg. The third group was injected with anti-CTLA4 antibody clone 9D9 (IgG2b) i.p. dosed at 1.5 mg/kg. The fourth group was injected with anti-CTLA4 antibody clone 9D9 (IgG2b) i.p. dosed at 10 mg/kg. Tumors were measured on day 10, 13, 17, 19, 21, 24.

At day 21 (when all the controls were still in the study), treatment with murine CD80 ECD-Fc at 20 mol/mol SA dosed at 0.3 mg/kg resulted in 90% inhibition of tumor growth compared to the control (P<0.001). Treatment with anti-CTLA4 antibody at 10 mg/kg resulted in 75% inhibition of tumor growth compared to the control (P<0.001). By comparison, treatment with anti-CTLA4 antibody at 1.5 mg/kg only induced 53% inhibition of tumor growth (P<0.001) (FIG. 7). At day 21, the impact of treatment with murine CD80 ECD-Fc at 20 mol/mol SA dosed at 0.3 mg/kg on tumor growth was significantly greater than anti-CTLA4 antibody dosed at 1.5 mg/kg (P<0.001) or at 10 mg/kg (P=0.009).

The incidence of tumor-free mice was analyzed at day 37. Treatment with murine CD80 ECD-Fc at 20 mol/mol SA dosed at 0.3 mg/kg led to complete tumor regression in 7/15 (47%) of the mice. Treatment with anti-CTLA4 antibody at 10 mg/kg led to complete tumor regression in 3/15 (20%) of the mice. None of the mice treated with anti-CTLA4 antibody at 1.5 mg/kg had complete tumor regression.

MC38 Tumor Model

Seven week old female C57Bl/6 mice were purchased from Charles River Laboratories (Hollister, Calif.) and were acclimated for one week before the study was initiated. The murine colorectal carcinoma cell line MC38 was implanted subcutaneously over the right flank of the mice at $0.5\times10^6$ cells/100 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and matrigel.

Mice were monitored twice weekly following cell implantation for tumor growth. For tumor measurements, the length and width of each tumor was measured using calipers and volume was calculated according to the formula: tumor volume $(mm^3)=(width\ (mm)\times length\ (mm))^2/2$. On Day 7, all tumors were measured, and mice were randomly assigned to seven treatment groups (n=15 mice per experimental group). The mean tumor volume for all animals enrolled was 78 $mm^3$. Mice were dosed 3 times, on day 7, 10 and 14. The first group was injected with mouse IgG2b (mIgG2b) i.p. dosed at 10 mg/kg (control). The second group was injected with murine CD80 ECD-Fc 20 mol/mol SA i.v. dosed at 3 mg/kg. The third group was injected with anti-CTLA4 antibody clone 9D9 (IgG2b) i.p. dosed at 1.5 mg/kg. The fourth group was injected with anti-CTLA4 antibody clone 9D9 (IgG2b) i.p. dosed at 10 mg/kg. Tumors were measured on day 11, 14, 17, and 19.

At day 19 (when all the controls were still in the study), treatment with murine CD80 ECD-Fc at 20 mol/mol SA dosed at 3 mg/kg resulted in 79% inhibition of tumor growth compared to the control (P<0.001). Moreover, murine CD80 ECD-Fc at 20 mol/mol SA had a greater impact on tumor growth compared to anti-CTLA4 antibody (P<0.001). Treatment with anti-CTLA4 antibody at 10 mg/kg reduced tumor growth by 21% compared to the control (P=0.05) while at 1.5 mg/kg did not significantly affect tumor size (FIG. 8). At day 21, the impact of treatment with murine CD80 ECD-Fc at 20 mol/mol SA dosed at 3 mg/kg on tumor growth was significantly greater than anti-CTLA4 antibody dosed at 1.5 mg/kg (P<0.001) or at 10 mg/kg (P=0.009).

While a 3 mg/kg dose of CD80 ECD-Fc was used for these experiments, a 0.3 mg/kg dose of CD80 ECD-Fc also reduced tumor cell growth in the MC38 tumor model (data not shown).

B16 Tumor Model

Seven week old female C57Bl/6 mice were purchased from Charles River Laboratories (Hollister, Calif.) and were acclimated for one week before the study was initiated. The murine melanoma cell line B16-F10 was implanted subcutaneously over the right flank of the mice at $0.5 \times 10^6$ cells/100 μl/mouse. Prior to inoculation, the cells were cultured for no more than three passages in DMEM medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free DMEM and matrigel.

Mice were monitored twice weekly following cell implantation for tumor growth. For tumor measurements, the length and width of each tumor was measured using calipers and volume was calculated according to the formula: tumor volume $(mm^3)$=(width (mm)×length $(mm))^2/2$. On Day 7, all tumors were measured, and mice were randomly assigned to seven treatment groups (n=15 mice per experimental group). The mean tumor volume for all animals enrolled was 70 $mm^3$. Mice were dosed 3 times, on day 3, 6 and 10. The first group was injected with mouse IgG2b (mIgG2b) dosed i.p. at 10 mg/kg (control). The second group was injected with murine CD80 ECD-Fc 20 mol/mol SA i.v. dosed at 3 mg/kg. The third group was injected with anti-CTLA4 antibody clone 9D9 (IgG2b) i.p. dosed at 1.5 mg/kg. The fourth group was injected with anti-CTLA4 antibody clone 9D9 (IgG2b) i.p. dosed at 10 mg/kg. Tumors were measured on day 10, 13, 15, 16, 17.

At day 13 (when all the controls were still in the study) treatment with murine CD80 ECD-Fc at 20 mol/mol SA dosed at 3 mg/kg resulted in 41% inhibition of tumor growth compared to the control (P<0.001). Treatment with anti-CTLA4 antibody at 10 mg/kg or 1.5 mg/kg did not significantly affect tumor growth compared to the control (FIG. 9).

TABLE OF SEQUENCES

| SEQ. ID. NO. | Description | Sequence |
| --- | --- | --- |
| 1 | Human CD80 precursor (with signal sequence) amino acid sequence | MGHTRRQGTSPSKCPYLNFFQLLVLAGLSHFCSGVIHVTKEVKE VATLSCGHNVSVEELAQTRIYWQKEKKMVLTMMSGDMNIWPEYK NRTIFDITNNLSIVILALRPSDEGTYECVVLKYEKDAFKREHLA EVTLSVKADFPTPSISDFEIPTSNIRRIICSTSGGFPEPHLSWL ENGEELNAINTTVSQDPETELYAVSSKLDFNMTTNHSFMCLIKY GHLRVNQTFNWNTTKQEHFPDNLLPSWAITLISVNGIFVICCLT YCFAPRCRERRRNERLRRESVRPV |
| 2 | Mouse CD80 precursor (with signal sequence) amino acid sequence | MACNCQLMQDTPLLKFPCPRLILLFVLLIRLSQVSSDVDEQLSK SVKDKVLLPCRYNSPHEDESEDRIYWQKHDKVVLSVIAGKLKVW PEYKNRTLYDNTTYSLIILGLVLSDRGTYSCVVQKKERGTYEVK HLALVKLSIKADFSTPNITESGNPSADTKRITCFASGGFPKPRF SWLENGRELPGINTTISQDPESELYTISSQLDFNTTRNHTIKCL IKYGDAHVSEDFTWEKPPEDPPDSKNTLVLFGAGFGAVITVVVI VVIIKCFCKHRSCFRRNEASRETNNSLTFGPEEALAEQTVFL |
| 3 | Human CD80 Isoform 2 (without signal sequence) | VIHVTKEVKEVATLSCGHNVSVEELAQTRIYWQKEKKMVLTMMS GDMNIWPEYKNRTIFDITNNLSIVILALRPSDEGTYECVVLKYE KDAFKREHLAEVTLSVKADFPTPSISDFEIPTSNIRRIICSTSG GFPEPHLSWLENGEELNAINTTVSQDPETELYAVSSKLDFNMTT NHSFMCLIKYGHLRVNQTFNWNTSFAPRCRERRRNERLRRESVR PV |
| 4 | Human CD80 Isoform 3 (without signal sequence) | VIHVTKEVKEVATLSCGHNVSVEELAQTRIYWQKEKKMVLTMMS GDMNIWPEYKNRTIFDITNNLSIVILALRPSDEGTYECVVLKYE KDAFKREHLAEVTLSVKGFAPRCRERRRNERLRRESVRPV |
| 5 | Human CD80 ECD sequence (without signal sequence) | VIHVTKEVKEVATLSCGHNVSVEELAQTRIYWQKEKKMVLTMMS GDMNIWPEYKNRTIFDITNNLSIVILALRPSDEGTYECVVLKYE KDAFKREHLAEVTLSVKADFPTPSISDFEIPTSNIRRIICSTSG GFPEPHLSWLENGEELNAINTTVSQDPETELYAVSSKLDFNMTT NHSFMCLIKYGHLRVNQTFNWNTTKQEHFPDN |
| 6 | Mouse CD80 ECD sequence (without signal sequence) | VDEQLSKSVKDKVLLPCRYNSPHEDESEDRIYWQKHDKVVLSVI AGKLKVWPEYKNRTLYDNTTYSLIILGLVLSDRGTYSCVVQKKE RGTYEVKHLALVKLSIKADFSTPNITESGNPSADTKRITCFASG GFPKPRFSWLENGRELPGINTTISQDPESELYTISSQLDFNTTR NHTIKCLIKYGDAHVSEDFTWEKPPEDPPDSKN |
| 7 | Human CD80 signal sequence | MGHTRRQGTSPSKCPYLNFFQLLVLAGLSHFCSG |
| 8 | Mouse CD80 signal sequence | MACNCQLMQDTPLLKFPCPRLILLFVLLIRLSQVSSD |

TABLE OF SEQUENCES-continued

| SEQ. ID. NO. | Description | Sequence |
|---|---|---|
| 9 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 10 | Fc | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 11 | Fc | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 12 | Human IgG1 Fc L234F, L235E, P331S mutant | EPKSSDKTHTCPPCPAPEFEGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPASIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGK |
| 13 | Human IgG1 Fc N297 mutant | EPKSSDKTHTCPPCPAPELLGGPSVFLFPPKPKDTLMISRTPEV TCVVVDVSHEDPEVKFNWYVDGVEVHNAKTKPREEQYGSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGK |
| 14 | Fc human IgG1 | EPKSSDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGK |
| 15 | Fc human IgG3 | ELKTPLGDTTHTCPRCPEPKSCDTPPPCPRCPEPKSCDTPPPCP RCPEPKSCDTPPPCPRCPAPELLGGPSVFLFPPKPKDTLMISRT PEVTCVVVDVSHEDPEVQFKWYVDGVEVHNAKTKPREEQYNSTF RVVSVLTVLHQDWLNGKEYKCKVSNKALPAPIEKTISKTKGQPR EPQVYTLPPSREEMTKNQVSLTCLVKGFYPSDIAVEWESSGQPE NNYNTTPPMLDSDGSFFLYSKLTVDKSRWQQGNIFSCSVMHEAL HNRFTQKSLSLSPGK |
| 16 | Fc human IgG4 | ESKYGPPCPPCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLGK |
| 17 | Mouse CD80 ECD mouse Fc IgG1 (Fc portion underlined) | VDEQLSKSVKDKVLLPCRYNSPHEDESEDRIYWQKHDKVVLSVI AGKLKVWPEYKNRTLYDNTTYSLIILGLVLSDRGTYSCVVQKKE RGTYEVKHLALVKLSIKADFSTPNITESGNPSADTKRITCFASG GFPKPRFSWLENGRELPGINTTISQDPESELYTISSQLDFNTTR NHTIKCLIKYGDAHVSEDFTWEKPPEDPPDSK<u>EPRGPTIKPCP PCKCPAPNLLGGPSVFIFPPKIKDVLMISLSPIVTCVVVDVSED DPDVQISWFVNNVEVHTAQTQTHREDYNSTLRVVSALPIQHQDW MSGKEFKCKVNNKDLPAPIERTISKPKGSVRAPQVYVLPPPEEE MTKKQVTLTCMVTDFMPEDIYVEWTNNGKTELNYKNTEPVLDSD GSYFMYSKLRVEKKNWVERNSYSCSVVHEGLHNHHTTKSFSRTP GK</u> |
| 18 | Mouse CD80 ECD Human Fc IgG1 WT (Fc portion underlined) | VDEQLSKSVKDKVLLPCRYNSPHEDESEDRIYWQKHDKVVLSVI AGKLKVWPEYKNRTLYDNTTYSLIILGLVLSDRGTYSCVVQKKE RGTYEVKHLALVKLSIKADFSTPNITESGNPSADTKRITCFASG GFPKPRFSWLENGRELPGINTTISQDPESELYTISSQLDFNTTR NHTIKCLIKYGDAHVSEDFTWEKPPEDPPDSKN<u>EPKSSDKTHTC PPCPAPELLGGPSVFLFPPKPKDTLMISRTPEVTCVVVDVSHED PEVKFNWYVDGVEVHNAKTKPREEQYNSTYRVVSVLTVLHQDWL</u> |

TABLE OF SEQUENCES-continued

| SEQ. ID. NO. | Description | Sequence |
|---|---|---|
|  |  | NGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSPG<br>K |
| 19 | Mouse CD80 ECD Fc IgG1 MT (234, 235, 331) (Fc portion underlined; mutants shown in bold) | VDEQLSKSVKDKVLLPCRYNSPHEDESEDRIYWQKHDKVVLSVI<br>AGKLKVWPEYKNRTLYDNTTYSLIILGLVLSDRGTYSCVVQKKE<br>RGTYEVKHLALVKLSIKADFSTPNITESGNPSADTKRITCFASG<br>GFPKPRFSWLENGRELPGINTTISQDPESELYTISSQLDFNTTR<br>NHTIKCLIKYGDAHVSEDFTWEKPPEDPPDSKN<u>EPKSSDKTHTC<br>PPCPAPEFEGGPSVFLFPPKPKDTLMISRTPEVTCVVVDVSHED<br>PEVKFNWYVDGVEVHNAKTKPREEQYNSTYRVVSVLTVLHQDWL<br>NGKEYKCKVSNKALPASIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSPG<br>K</u> |
| 20 | Human CD80 ECD Human Fc IgG1 WT (Fc portion underlined) | VIHVTKEVKEVATLSCGHNVSVEELAQTRIYWQKEKKMVLTMMS<br>GDMNIWPEYKNRTIFDITNNLSIVILALRPSDEGTYECVVLKYE<br>KDAFKREHLAEVTLSVKADFPTPSISDFEIPTSNIRRIICSTSG<br>GFPEPHLSWLENGEELNAINTTVSQDPETELYAVSSKLDFNMTT<br>NHSFMCLIKYGHLRVNQTFNWNTTKQEHFPDN<u>EPKSSDKTHTCP<br>PCPAPELLGGPSVFLFPPKPKDTLMISRTPEVTCVVVDVSHEDP<br>EVKFNWYVDGVEVHNAKTKPREEQYNSTYRVVSVLTVLHQDWLN<br>GKEYKCKVSNKALPAPIEKTISKAKGQPREPQVYTLPPSRDELT<br>KNQVSLTCLVKGFYPSDIAVEWESNGQPENNYKTTPPVLDSDGS<br>FFLYSKLTVDKSRWQQGNVFSCSVMHEALHNHYTQKSLSLSPGK</u> |
| 21 | Human CD80 ECD Human Fc IgG1 L234F, L235E, P331S MT (Fc portion underlined; mutants in bold) | VIHVTKEVKEVATLSCGHNVSVEELAQTRIYWQKEKKMVLTMMS<br>GDMNIWPEYKNRTIFDITNNLSIVILALRPSDEGTYECVVLKYE<br>KDAFKREHLAEVTLSVKADFPTPSISDFEIPTSNIRRIICSTSG<br>GFPEPHLSWLENGEELNAINTTVSQDPETELYAVSSKLDFNMTT<br>NHSFMCLIKYGHLRVNQTFNWNTTKQEHFPDN<u>EPKSSDKTHTCP<br>PCPAPEFEGGPSVFLFPPKPKDTLMISRTPEVTCVVVDVSHEDP<br>EVKFNWYVDGVEVHNAKTKPREEQYNSTYRVVSVLTVLHQDWLN<br>GKEYKCKVSNKALPASIEKTISKAKGQPREPQVYTLPPSRDELT<br>KNQVSLTCLVKGFYPSDIAVEWESNGQPENNYKTTPPVLDSDGS<br>FFLYSKLTVDKSRWQQGNVFSCSVMHEALHNHYTQKSLSLSPGK</u> |
| 22 | human PD-1 precursor (with signal sequence) UniProtKB/ Swiss-Prot: Q15116.3, 01-OCT.-2014 | MQIPQAPWPV VWAVLQLGWR PGWFLDSPDR PWNPPTFSPA<br>LLVVTEGDNA TFTCSFSNTS ESFVLNWYRM SPSNQTDKLA<br>AFPEDRSQPG QDCRFRVTQL PNGRDFHMSV VRARRNDSGT<br>YLCGAISLAP KAQIKESLRA ELRVTERRAE VPTAHPSPSP<br>RPAGQFQTLV VGVVGGLLGS LVLLVWVLAV ICSRAARGTI<br>GARRTGQPLK EDPSAVPVFS VDYGELDFQW REKTPEPPVP<br>CVPEQTEYAT IVFPSGMGTS SPARRGSADG PRSAQPLRPE<br>DGHCSWPL |
| 23 | human PD-1 (mature, without signal sequence) | PGWFLDSPDR PWNPPTFSPA LLVVTEGDNA TFTCSFSNTS<br>ESFVLNWYRM SPSNQTDKLA AFPEDRSQPG QDCRFRVTQL<br>PNGRDFHMSV VRARRNDSGT YLCGAISLAP KAQIKESLRA<br>ELRVTERRAE VPTAHPSPSP RPAGQFQTLV VGVVGGLLGS<br>LVLLVWVLAV ICSRAARGTI GARRTGQPLK EDPSAVPVFS<br>VDYGELDFQW REKTPEPPVP CVPEQTEYAT IVFPSGMGTS<br>SPARRGSADG PRSAQPLRPE DGHCSWPL |
| 24 | human PD-L1 precursor (with signal sequence) UniProtKB/ Swiss-Prot: Q9NZQ7.1, 01-OCT.-2014 | MRIFAVFIFM TYWHLLNAFT VTVPKDLYVV EYGSNMTIEC<br>KFPVEKQLDL AALIVYWEME DKNIIQFVHG EEDLKVQHSS<br>YRQRARLLKD QLSLGNAALQ ITDVKLQDAG VYRCMISYGG<br>ADYKRITVKV NAPYNKINQR ILVVDPVTSE HELTCQAEGY<br>PKAEVIWTSS DHQVLSGKTT TTNSKREEKL FNVTSTLRIN<br>TTTNEIFYCT FRRLDPEENH TAELVIPELP LAHPPNERTH<br>LVILGAILLC LGVALTFIFR LRKGRMMDVK KCGIQDTNSK<br>KQSDTHLEET |
| 25 | human PD-L1 (mature, without signal sequence) | FT VTVPKDLYVV EYGSNMTIEC KFPVEKQLDL<br>AALIVYWEME DKNIIQFVHG EEDLKVQHSS YRQRARLLKD<br>QLSLGNAALQ ITDVKLQDAG VYRCMISYGG ADYKRITVKV<br>NAPYNKINQR ILVVDPVTSE HELTCQAEGY PKAEVIWTSS<br>DHQVLSGKTT TTNSKREEKL FNVTSTLRIN TTTNEIFYCT<br>FRRLDPEENH TAELVIPELP LAHPPNERTH LVILGAILLC<br>LGVALTFIFR LRKGRMMDVK KCGIQDTNSK KQSDTHLEET |

The table below provides a listing of certain sequences referenced herein.

What is claimed is:

1. A CD80 extracellular domain (ECD) fusion molecule comprising the amino acid sequence of SEQ ID NO:20, wherein the CD80 ECD fusion molecule comprises 15-60 molecules of sialic acid (SA).

2. The fusion molecule of claim 1, wherein the fusion molecule comprises 15-40 molecules of SA.

3. The fusion molecule of claim 1, wherein the fusion molecule comprises 15-30 molecules of SA.

4. The fusion molecule of claim 1, wherein the fusion molecule comprises 20-30 molecules of SA.

5. The fusion molecule of claim 1, wherein the fusion molecule alone does not cause significant release of interferon gamma or TNF alpha from T-cells in vitro.

6. The fusion molecule of claim 1, wherein the fusion molecule alone causes less release of interferon gamma or TNF alpha from T-cells in vitro than TGN1412 alone.

7. The fusion molecule of claim 6, wherein the fusion molecule alone is at least 1000-fold less potent at inducing interferon gamma or TNF alpha release compared to TGN1412 alone.

8. The fusion molecule of claim 1, wherein the fusion molecule is capable of at least 90% tumor growth inhibition in at least one mouse syngeneic cancer model over a period of at least 1 week, 10 days, two weeks, or three weeks following administration of a single dose of the fusion molecule at 0.3 to 0.6 mg/kg.

9. The fusion molecule of claim 8, wherein the mouse syngeneic cancer model is a CT26 tumor model.

10. A composition comprising (i) fusion molecules comprising the amino acid sequence of SEQ ID NO:20 and (ii) at least one pharmaceutically acceptable carrier, wherein the CD80 ECD fusion molecules comprise 15-60 moles of SA per mole of CD80 ECD fusion protein.

11. The composition of claim 10, wherein the CD80 ECD fusion molecules comprise 15-40 moles of SA per mole of CD80 ECD fusion protein.

12. The composition of claim 10, wherein the CD80 ECD fusion molecules comprise 15-30 moles of SA per mole of CD80 ECD fusion protein.

13. The composition of claim 10, wherein the CD80 ECD fusion molecules comprise 20-30 moles of SA per mole of CD80 ECD fusion protein.

14. The composition of claim 10, wherein the CD80 ECD fusion molecules comprise at least 20 moles of SA per mole of CD80 ECD fusion protein.

15. The composition of claim 10, wherein the composition alone does not cause significant release of interferon gamma or TNF alpha from T-cells in vitro.

16. The composition of claim 10, wherein the composition alone causes less release of interferon gamma or TNF alpha from T-cells in vitro than TGN1412 alone.

17. The composition of claim 16, wherein the composition alone is at least 1000-fold less potent at inducing interferon gamma or TNF alpha release compared to TGN1412 alone.

18. The composition of claim 11, wherein the composition alone does not cause significant release of interferon gamma or TNF alpha from T-cells in vitro.

19. The composition of claim 11, wherein the composition alone causes less release of interferon gamma or TNF alpha from T-cells in vitro than TGN1412 alone.

20. The composition of claim 19, wherein the composition alone is at least 1000-fold less potent at inducing interferon gamma or TNF alpha release compared to TGN1412 alone.

21. The composition of claim 10, wherein the composition is capable of at least 90% tumor growth inhibition in at least one mouse syngeneic cancer model over a period of at least one week, 10 days, two weeks, or three weeks following administration of a single dose of the composition at 0.3 to 0.6 mg/kg.

22. The composition of claim 21, wherein the mouse syngeneic cancer model is a CT26 tumor model.

23. A CD80 ECD fusion molecule comprising the amino acid sequence of SEQ ID NO: 21.

24. A composition comprising (i) CD80 ECD fusion molecules comprising the amino acid sequence of SEQ ID NO:20, and (ii) at least one pharmaceutically acceptable carrier,
wherein the CD80 ECD fusion molecules comprise at least 15 moles of SA per mole of CD80 ECD fusion protein.

25. The composition of claim 24, wherein the CD80 ECD fusion molecules comprise at least 20 moles of SA per mole of CD80 ECD fusion protein.

26. The composition of claim 24, wherein the composition alone does not cause significant release of interferon gamma or TNF alpha from T-cells in vitro.

27. The composition of claim 24, wherein the composition alone causes less release of interferon gamma or TNF alpha from T-cells in vitro than TGN1412 alone.

28. The composition of claim 27, wherein the composition alone is at least 1000-fold less potent at inducing interferon gamma or TNF alpha release compared to TGN1412 alone.

29. The composition of claim 24, wherein the composition is capable of at least 90% tumor growth inhibition in the mouse CT26 tumor model over a period of at least one week, 10 days, two weeks, or three weeks following administration of a single dose of the composition at 0.3 to 0.6 mg/kg.

30. The composition of claim 14, wherein the composition alone does not cause significant release of interferon gamma or TNF alpha from T-cell in vitro.

31. The composition of claim 14, wherein the composition alone causes less release of interferon gamma or TNF alpha from T-cells in vitro than TGN1412 alone.

32. The composition of claim 31, wherein the composition alone is at least 1000-fold less potent at inducing interferon gamma or TNF alpha release compared to TGN1412 alone.

33. The composition of claim 14, wherein the composition is capable of at least 90% tumor growth inhibition in the mouse CT26 tumor model over a period of at least one week, 10 days, two weeks, or three weeks following administration of a single dose of the composition at 0.3 to 0.6 mg/kg.

34. The composition of claim 11, wherein the composition is capable of at least 90% tumor growth inhibition in the mouse CT26 tumor model over a period of at least one week, 10 days, two weeks, or three weeks following administration of a single dose of the composition at 0.3 to 0.6 mg/kg.

35. A CD80 extracellular domain (ECD) fusion molecule comprising the amino acid sequence of SEQ ID NO:20.

36. The fusion molecule of claim 35, wherein the fusion molecule alone does not cause significant release of interferon gamma or TNF alpha from T-cells in vitro.

37. The fusion molecule of claim 35, wherein the fusion molecule alone causes less release of interferon gamma or TNF alpha from T-cells in vitro than TGN1412 alone.

38. The fusion molecule of claim 37, wherein the fusion molecule alone is at least 1000-fold less potent at inducing interferon gamma or TNF alpha release compared to TGN1412 alone.

39. The fusion molecule of claim 35, wherein the fusion molecule is capable of at least 90% tumor growth inhibition in at least one mouse syngeneic cancer model over a period of at least 1 week, 10 days, two weeks, or three weeks following administration of a single dose of the fusion molecule at 0.3 to 0.6 mg/kg.

40. The fusion molecule of claim 39, wherein the mouse syngeneic cancer model is a CT26 tumor model.

\* \* \* \* \*

UNITED STATES PATENT AND TRADEMARK OFFICE
CERTIFICATE OF CORRECTION

PATENT NO. : 10,273,281 B2
APPLICATION NO. : 15/340238
DATED : April 30, 2019
INVENTOR(S) : Brennan et al.

Page 1 of 1

It is certified that error appears in the above-identified patent and that said Letters Patent is hereby corrected as shown below:

In the Claims

In Claim 10, at Column 89, Line 9, change "(i) fusion molecules" to -- (i) CD80 ECD fusion molecules --.
In Claim 30, at Column 90, Line 22, change "T-cell" to -- T-cells --.

Signed and Sealed this
Ninth Day of July, 2019

Andrei Iancu
*Director of the United States Patent and Trademark Office*